(12) United States Patent
Lavergne et al.

(10) Patent No.: US 6,887,869 B2
(45) Date of Patent: May 3, 2005

(54) MIKANOLIDE DERIVATIVES, THEIR PREPARATION AND THERAPEUTIC USES

(75) Inventors: Olivier Lavergne, Palaiseau (FR); Christophe Lanco, Dourdan (FR); Grégoire Prevost, Antony (FR); Beng Poon Teng, Gif-sur-Yvette (FR)

(73) Assignee: Societe de Conseils de Recherches et d'Applications Scientifiques (S.C.R.A.S.) (FR)

( * ) Notice: Subject to any disclaimer, the term of this patent is extended or adjusted under 35 U.S.C. 154(b) by 0 days.

(21) Appl. No.: 10/250,383

(22) PCT Filed: Jan. 11, 2002

(86) PCT No.: PCT/FR02/00092

§ 371 (c)(1),
(2), (4) Date: Jun. 25, 2003

(87) PCT Pub. No.: WO02/055523

PCT Pub. Date: Jul. 18, 2002

(65) Prior Publication Data

US 2004/0122084 A1 Jun. 24, 2004

(30) Foreign Application Priority Data

Jan. 12, 2001 (FR) .......................... 01 00397
Nov. 14, 2001 (FR) .......................... 01 14688

(51) Int. Cl.⁷ .................. A61K 31/34; C07D 493/08; C07D 493/22
(52) U.S. Cl. .................. 514/232.8; 514/321; 514/409; 514/443; 514/444; 514/468; 544/148; 546/197; 548/409; 548/494; 549/57; 549/60; 549/267; 549/297; 549/298
(58) Field of Search ................ 549/267, 297, 549/298, 57, 60; 544/148, 546; 546/197; 548/409, 494; 514/232.8, 321, 409, 443, 444, 468

(56) References Cited

FOREIGN PATENT DOCUMENTS

FR 2801792 6/2001

OTHER PUBLICATIONS

Kupchan et al, "The ... *Elephantopus elatus*", Journal of the American Chemical Society, vol. 88, No. 15, 1966 pp. 3674–3676.
Facey et al, Investigation . . . Pharmacology, Journal of Pharmacy and Pharmacology, London, GB, vol. 51, 1999, pp. 1455–1460.

*Primary Examiner*—Bernard I. Dentz
(74) *Attorney, Agent, or Firm*—Muserlian, Lucas and Mercanti

(57) ABSTRACT

The invention concerns novel mikanolide derivatives, their preparation method and their therapeutic uses, in particular as anti-cancer and anti-viral agents. The compounds correspond to general formula (1) corresponding to general sub-formulae $(I)_1$ and $(I)_2$, wherein: $R_1$ represents H, $SR_4$ or $NR_4R_5$; $R_2$ represents $SR_6$ or $NR_6R_7$; $R_3$ represents OH, $O(CO)R_{14}$, $OSiR_{15}R_{16}R_{17}$, $O(CO)OR_{18}$ or $O(CO)NHR_{18}$, each of the radicals $R_4$, $R_6$, $R_{15}$, $R_{16}$ and $R_{17}$ representing independently (in particular) an alkyl radical, the radicals $R_5$ and $R_7$ representing (in particular) radicals selected independently among a hydrogen atom and an alkyl radical, and each of the radicals $R_{14}$ and $R_{18}$ representing independently (in particular) an alkyl or cycloalkyl radical, or one among aryl, heteroaryl, aralkyl or heteroalkyl radicals optionally substituted; provided that when the compounds correspond to the general sub-formula $(I)_2$, then $R_1$ does not represent a hydrogen atom

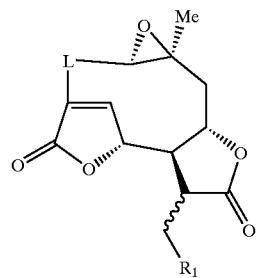

(I)

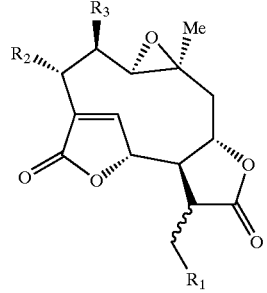

$(I)_1$

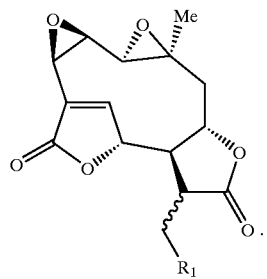

$(I)_2$

13 Claims, No Drawings

MIKANOLIDE DERIVATIVES, THEIR PREPARATION AND THERAPEUTIC USES

This application is a 371 of PCT/FR02/00092 filed Jan. 11, 2002.

A subject of the invention is new derivatives of mikanolide, their preparation processes as well as their therapeutic uses, in particular as anticancerous, antibacterial and antiviral agents.

Tropical plants of the *Mikania* genus such as *M. cordata*, *M. scandens* or *M. micrantha* are part of certain traditional pharmacopeia of India, South America and Central America. Under the names of guaco, bejuco de finca, cepu, liane francois, matafinca, or also vedolin, the extracts of *Mikania* are used as antibiotics and anti-inflammatories.

Active substances originating from extracts of *Mikania* have been isolated and characterized: these are mikanolide and dihydromikanolide (see their structures in the figure below), and to a lesser extent scandenolides. These are sesquiterpenes of the germacrane family, i.e. having 4-isopropyl-1,7-dimethylcyclodecane as a hydrocarbon skeleton (Herz et al., *Tetrahedron Lett.* (1967) 3111–3115; Kiang et al., *Phytochemistry* (1968) 7: 1035–1037; Cuenca et al., *J. Nat. Prod.* (1988), 51, 625–626).

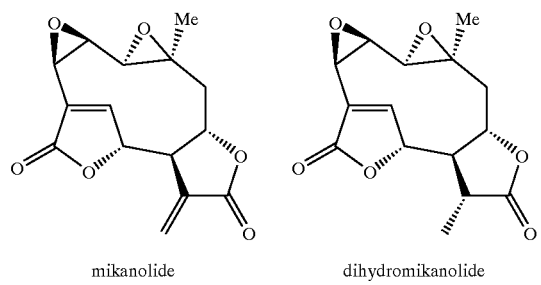

mikanolide          dihydromikanolide

Studies of the extracts of *Mikania* report an antimicrobial activity against *Staphylococus aureus* and *Candida albicans* (Facey et al., *J. Pharm. Pharmacol.* (1999) 51, 1455–1460; Mathur et al., *Rev. Latinoam. Quim.* (1975), 6, 201–205). Molluscicidal, piscicidal and bactericidal activities have also been described for dihydromikanolide (Vasquez et al., A G Meeting, Amsterdam, Netherlands, 26–30 Jul. 1999, poster No. 316).

For the purpose of elucidating structures, certain simple derivatives of mikanolide and dihydromikanolide, and in particular the compounds of general formulae (A1) and (A2) represented below

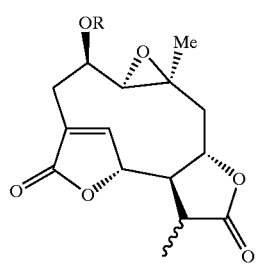

(A1)

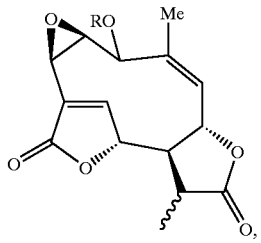

(A2)

in which R represents a hydrogen atom or the acetyl group, have been synthesized and described in Herz et al., *J. Org. Chem.* (1970), 35, 1453–1464. However, no pharmacological activity has been disclosed for these compounds.

The Applicant recently described in PCT Patent Application WO 01/39720 that mikanolide and dihydromikanolide are endowed with an antiproliferative activity linked to the inhibition of DNA-polymerase. However, mikanolides do not possess all the physico-chemical properties desirable for medicamentous use as they are neither very water soluble, nor very stable, which renders their pharmaceutical use relatively difficult, in particular in injectable form.

The Applicant has now developed new semi-synthetic mikanolide derivatives, which can be used for the treatment of diseases due to abnormal cell proliferation, in particular for the treatment of cancer, viral diseases and bacterial and parasitic infections. These compounds have the advantage of better solubility and better stability than that of mikanolide and dihydromikanolide while retaining an activity similar to or even greater than that of the latter.

A subject of the invention is the compounds of general formula (I)

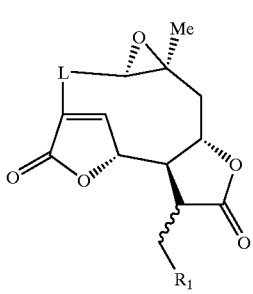

(I)

corresponding to general sub-formulae $(I)_1$ and $(I)_2$:

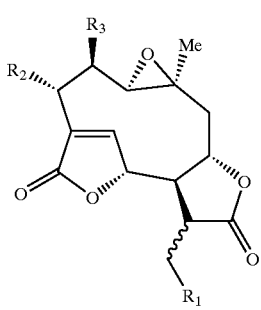

$(I)_1$

-continued

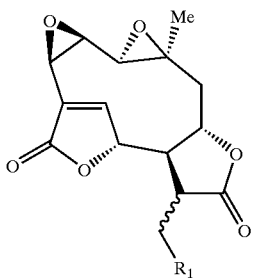

(I)₂ in which

R₁ represents a hydrogen atom or an SR₄ or NR₄R₅ radical;

R₂ represents SR₆ or NR₆R₇;

R₃ represents OH, O(CO)R₁₄, OSiR₁₅R₁₆R₁₇, O(CO)OR₁₈ or O(CO)NHR₁₈;

R₄ and R₆ represent, independently, an alkyl radical, a cycloalkyl, cycloalkylalkyl, hydroxyalkyl radical or also one of the aryl or aralkyl radicals optionally substituted on their aryl group by one or more radicals chosen from the alkyl, hydroxy or alkoxy radicals, R₅ and R₇ represent, independently, a hydrogen atom, an alkyl radical, a cycloalkyl, cycloalkylalkyl, hydroxyalkyl radical or also one of the aryl or aralkyl radicals optionally substituted on their aryl group by one or more radicals chosen from the alkyl, hydroxy or alkoxy radicals, R₄ and R₅ being able to form together with the nitrogen atom which carries them a heterocycle with 5 to 7 members, the additional members being chosen from the —CR₈R₉—, —NR₁₀—, —O— and —S— radicals, it being understood however that there can only be one member chosen from —O— or —S— in said heterocycle, and R₆ and R₇ being able to form together with the nitrogen atom which carries them a heterocycle with 5 to 7 members, the additional members being chosen from the —CR₁₁R₁₂—, —NR₁₃—, —O— and —S— radicals, it being understood however that there can only be one member chosen from —O— or —S— in said heterocycle, R₈, R₁₀, R₁₁ and R₁₃ represent, independently each time they are involved, a hydrogen atom or an alkyl, alkoxycarbonyl or aralkyl radical, R₉ and R₁₂ representing, independently each time they are involved, a hydrogen atom or each of R₉ and R₁₂ being able to form respectively together with R₈ and R₁₁ an —O—(CH₂)₂—O— radical attached on either side to the carbon atom which carries them, such a radical only being present however once at most per NR₄R₅ or NR₆R₇ radical, represent, independently each time they are involved, a hydrogen atom or an alkyl radical;

R₁₄ represents an alkyl, cycloalkyl or adamantyl radical or one of the aryl, heteroaryl, aralkyl or heteroaralkyl radicals optionally substituted on their aryl or heteroaryl group by one or more radicals chosen from a halogen atom and the alkyl, haloalkyl, nitro, hydroxy, alkoxy, alkylthio or phenyl radicals, or also R₁₄ is such that R₁₄—COOH represents a natural amino acid or the optical enantiomer of such an amino acid;

R₁₅, R₁₆ and R₁₇ represent, independently, an alkyl radical or a phenyl radical;

R₁₈ represents an alkyl, cycloalkyl or adamantyl radical or one of the aryl, heteroaryl, aralkyl or heteroaralkyl radicals optionally substituted on their aryl or heteroaryl group by one or more radicals chosen from a halogen atom and the alkyl, haloalkyl, nitro, hydroxy, alkoxy, alkylthio or phenyl radicals;

it being understood however that when the compounds correspond to general sub-formula (I)₂, then R₁ does not represent a hydrogen atom;

or the salts of the latter.

By alkyl, unless otherwise specified, is meant a linear or branched alkyl radical containing 1 to 12 carbon atoms, and preferably 1 to 6 carbon atoms. By cycloalkyl, unless otherwise specified, is meant a monocyclic carbon system containing 3 to 7 carbon atoms. By haloalkyl, is meant an alkyl radical at least one of the hydrogen atoms (and optionally all) of which is replaced by a halogen atom. By carbocyclic or heterocyclic aryl, unless otherwise specified, is meant a carbocyclic or heterocyclic system comprising one to three condensed rings at least one of which is an aromatic ring, a system being referred to as heterocyclic when at least one of the rings comprising it contains one or more heteroatoms (O, N or S). By aryl, unless otherwise specified, is meant a carbocyclic aryl radical. By heteroaryl is meant a heterocyclic aryl radical. By haloalkyl, is meant an alkyl radical at least one of the hydrogen atoms (and optionally all) of which is replaced by a halogen atom. Finally, by halogen atom is meant the fluorine, chlorine, bromine or iodine atoms.

By alkoxy, hydroxyalkyl, cycloalkylalkyl, aralkyl and heteroaralkyl radicals, is meant respectively the alkoxy, hydroxyalkyl, cycloalkylalkyl and aralkyl radicals the alkyl, cycloalkyl, aryl and heteroaralkyl radicals of which have the meanings indicated previously.

By natural amino acid, is understood valine (Val), leucine (Leu), isoleucine (Ile), methionine (Met), phenylalanine (Phe), asparagine (Asn), glutamic acid (Glu), glutamine (Gln), histidine (His), lysine (Lys), arginine (Arg), aspartic acid (Asp), glycine (Gly), alanine (Ala), serine (Ser), threonine (Thr), tyrosine (Tyr), tryptophane (Trp), cysteine (Cys) or proline (Pro).

By linear or branched alkyl having 1 to 6 carbon atoms, is meant in particular the methyl, ethyl, propyl, isopropyl, butyl, isobutyl, sec-butyl and tert-butyl, pentyl, neopentyl, isopentyl, hexyl, isohexyl radicals. By alkoxy, is meant in particular the methoxy, ethoxy and isopropoxy radicals, and in particular the methoxy and ethoxy radicals. By cycloalkyl is meant in particular the cyclopropyl, cyclobutyl, cyclopentyl and cyclohexyl radicals. By haloalkyl is meant in particular the trifluoromethyl radical. By carbocyclic aryl is meant in particular the phenyl, naphthyl and phenanthryl radicals, preferably the phenyl and naphthyl radicals and more preferentially the phenyl radical. By heterocyclic aryl is meant in particular the pyrrolyl, furanyl, benzofuranyl, thienyl, benzothienyl, pyridyl, pyrimidinyl, triazinyl, imidazolyl, oxazolyl, thiazolyl, indolyl and quinolyl radicals, and preferably the furanyl, benzofuranyl, thienyl and benzothienyl radicals. By aralkyl is meant in particular a phenalkyl radical, and preferably the benzyl radical. By heteroaralkyl is meant in particular a thienylalkyl, furanylalkyl, pyrrolylalkyl and thiazolylalkyl radical (the alkyl radical of said radicals being preferably a methyl radical), and preferably a thienylalkyl radical (preferably thienylmethyl).

A compound of general formula (I) having at least one of the following characteristics is preferred:

the compound corresponds to general sub-formula (I)₁;

R₁ represents a hydrogen atom or an NR₄R₅ radical;

R₂ represents an NR₆R₇ radical;

R₃ represents OH, or an O(CO)R₁₄, OSiR₁₅R₁₆R₁₇ or O(CO)NHR₁₈ radical.

More preferentially, a compound of general formula (I) will be such that it has at least one of the following characteristics:

the compound corresponds to general sub-formula $(I)_1$;
$R_1$ represents a hydrogen atom;
$R_2$ represents an $NR_6R_7$ radical;
$R_3$ represents AN $O(CO)R_{14}$, $OSiR_{15}R_{16}R_{17}$ or $O(CO)NHR_{18}$ radical.

Quite particularly, a compound of general formula (I) is such that it has at least one of the following characteristics:
the compound corresponds to general sub-formula $(I)_1$;
$R_1$ represents a hydrogen atom;
$R_2$ represents an $NR_6R_7$ radical and preferably an $NR_6R_7$ radical in which $R_6$ and $R_7$ are chosen independently from a hydrogen atom and an alkyl radical;
$R_3$ represents an $O(CO)R_{14}$, $OSiR_{15}R_{16}R_{17}$ or $O(CO)NHR_{18}$ radical.

Moreover, $R_2$ will quite preferentially represent an $NR_6R_7$ radical in which $R_6$ and $R_7$ are alkyl radicals, and in particular an $NR_6R_7$ radical in which $R_6$ and $R_7$ are methyl radicals. $R_3$ will quite preferentially represent an $O(CO)NHR_{18}$ radical.

Preferably also, $R_4$ will represent an alkyl or aralkyl radical, and $R_5$ will represent a hydrogen atom or an alkyl radical, or also $R_4$ and $R_5$ will form together with the nitrogen atom which carries them a heterocycle with 5 to 7 members, the additional members being chosen from the —$CR_8R_9$—, —$NR_{10}$—, —O— and —S— radicals. Preferably, $R_8$ will represent, independently each time it is involved, a hydrogen atom or an alkyl radical (and preferably a hydrogen atom) and $R_9$ will represent, independently each time it is involved, a hydrogen atom. Preferably, $R_{10}$ will represent, independently each time it is involved, a hydrogen atom or an alkyl radical.

Preferably also, $R_6$ will represent an alkyl or aralkyl radical, and $R_7$ will represent a hydrogen atom or an alkyl radical, or also $R_6$ and $R_7$ will form together with the nitrogen atom which carries them a heterocycle with 5 to 7 members, the additional members being chosen from the —$CR_{11}R_{12}$—, —$NR_{13}$—, —O— and —S— radicals. Preferably, $R_{11}$ will represent, independently each time it is involved, a hydrogen atom or an alkyl or alkoxycarbonyl radical (and preferably a hydrogen atom) or also $R_{11}$ and $R_{12}$ will represent, once together, an —O—$(CH_2)_2$—O— radical attached on either side to the carbon atom which carries it. Preferably, $R_{13}$ will represent, independently each time it is involved, a hydrogen atom or an alkyl radical.

Moreover, $R_{14}$ will preferably represent an alkyl or cycloalkyl radical, or one of the aryl or heteroaryl radicals optionally substituted by a halogen atom or a haloalkyl or phenyl radical. More preferentially, $R_{14}$ will represent a cycloalkyl radical or one of the aryl or heteroaryl radicals optionally substituted by a halogen atom or a haloalkyl radical. In a more preferred manner, $R_{14}$ will represent a cyclohexyl radical or one of the phenyl, thienyl or benzothienyl radicals optionally substituted by a halogen atom.

Finally, $R_{15}$, $R_{16}$ and $R_{17}$ will preferably represent alkyl radicals. In a particularly preferred manner, one of the $R_{15}$, $R_{16}$ and $R_{17}$ radicals will represent a tert-butyl radical and the other two will represent methyl radicals.

Finally, $R_{18}$ will preferably represent an alkyl, cycloalkyl or adamantyl radical, or one of the aryl or heteroaryl radicals optionally substituted by a halogen atom or an alkyl, haloalkyl, alkoxy, alkylthio or phenyl radical. More preferentially, $R_{18}$ will represent a cycloalkyl radical or one of the aryl or heteroaryl radicals optionally substituted by an alkyl, alkoxy or alkylthio radical. Still more preferably, $R_{18}$ will represent one of the phenyl, thienyl or benzothienyl radicals optionally substituted by an alkyl, alkoxy or alkylthio radical.

Moreover, when $R_4$ and $R_5$ form together with the nitrogen atom which carries them a heterocycle with 5 to 7 members, the $NR_4R_5$ radical preferably represents one of the pyrrolyl, piperidyl, piperazinyl, morpholinyl or thiomorpholinyl radicals optionally substituted by an alkyl radical (the latter being preferably a methyl or ethyl radical, and more preferentially a methyl radical) on one of its carbon or nitrogen atoms, or by an —O—$(CH_2)_2$—O— radical attached on either side to a carbon atom. More preferentially, when $R_4$ and $R_5$ form together with the nitrogen atom which carries them a heterocycle with 5 to 7 members, the $NR_4R_5$ radical will represent one of the pyrrolyl, piperidyl, piperazinyl, morpholinyl or thiomorpholinyl radicals optionally substituted by an alkyl radical (the latter being preferably a methyl radical) on one of its carbon or nitrogen atoms.

Similarly, when $R_6$ and $R_7$ form together with the nitrogen atom which carries them a heterocycle with 5 to 7 members, the $NR_6R_7$ radical preferably represents one of the pyrrolyl, piperidyl, piperazinyl, morpholinyl or thiomorpholinyl radicals optionally substituted by an alkyl radical (the latter preferably being a methyl or ethyl radical, and more preferentially a methyl radical) on one of its carbon or nitrogen atoms, or by an —O—$(CH_2)_2$—O— radical attached on either side to a carbon atom. More preferentially, when $R_6$ and $R_7$ form together with the nitrogen atom which carries them a heterocycle with 5 to 7 members, the $NR_6R_7$ radical will represent one of the pyrrolyl, piperidyl, piperazinyl, morpholinyl or thiomorpholinyl radicals optionally substituted by an alkyl radical (the latter preferably being a methyl radical) on one of its carbon or nitrogen atoms.

The invention relates in particular to the following compounds described in the examples:

12-diisopropylaminomethyl-7-methyl-3,6,10,15-tetraoxapentacyclo $[12.2.1.0^{2,4}.0^{5,7}.0^{9,13}]$heptadec-1(17)-ene-11,16-dione;

12-dimethylamino-3-dimethylaminomethyl-11-hydroxy-8-methyl-5,9,15-trioxatetracyclo$[11.2.1.0^{2,6}.0^{8,10}]$hexadec-13(16)-ene-4,14-dione;

12-benzyl(methyl)amino-3-benzyl(methyl)aminomethyl-11-hydroxy-8-methyl-5,9,15-trioxatetracyclo$[11.2.1.0^{2,6}.0^{8,10}]$hexadec-13(16)-ene-4,14-dione;

11-hydroxy-8-methyl-12-morpholino-3-morpholinomethyl-5,9,15-trioxatetracyclo$[11.2.1.0^{2,6}.0^{8,10}]$hexadec-13(16)-ene-4,14-dione;

12-dimethylamino-11-hydroxy-3,8-dimethyl-5,9,15-trioxatetracyclo$[11.2.1.0^{2,6}.0^{8,10}]$hexadec-13(16)-ene-4,14-dione;

11-hydroxy-3,8-dimethyl-12-(4-methylpiperidino)-5,9,15-trioxatetracyclo$[11.2.1.0^{2,6}.0^{8,10}]$hexadec-13(16)-ene-4,14-dione;

11-hydroxy-3,8-dimethyl-12-pyrrolidino-5,9,15-trioxatetracyclo$[11.2.1.0^{2,6}.0^{8,10}]$hexadec-13(16)-ene-4,14-dione;

ethyl 1-[11-hydroxy-3,8-dimethyl-4,14-dioxo-5,9,15-trioxatetracyclo$[11.2.1.0^{2,6}.0^{8,10}]$hexadec-13(16)-en-12-yl]-4-piperidinecarboxylate;

12-(4-benzylpiperidino)-11-hydroxy-3,8-dimethyl-5,9,15-trioxatetracyclo$[11.2.1.0^{2,6}0^{8,10}]$hexadec-13(16)-ene-4,14-dione;

11-hydroxy-3,8-dimethyl-12-piperidino-5,9,15-trioxatetracyclo$[11.2.1.0^{2,6}.0^{8,10}]$hexadec-13(16)-ene-4,14-dione;

12-(1,4-dioxa-8-azaspiro[4.5]dec-8-yl)-11-hydroxy-3,8-dimethyl-5,9,15-trioxatetracyclo$[11.2.1.0^{2,6}.0^{8,10}]$hexadec-13(16)-ene-4,14-dione;

11-hydroxy-3,8-dimethyl-12-morpholino-5,9,15-trioxatetracyclo[11.2.1.0$^{2,6}$.0$^{8,10}$]hexadec-13(16)-ene-4,14-dione;

11-(tert-butyldimethylsiloxy)-12-dimethylamino-3,8-dimethyl-5,9,15-trioxatetracyclo[11.2.1.0$^{2,6}$.0$^{8,10}$]hexadec-13(16)-ene-4,14-dione;

3,8-dimethyl-12-(4-methylpiperidino)-4,14-dioxo-5,9,15-trioxatetracyclo[11.2.1.0$^{2,6}$.0$^{8,10}$]hexadec-13(16)-en-11-yl acetate;

3,8-dimethyl-12-(4-methylpiperidino)-4,14-dioxo-11-phenylcarbonyloxy-5,9,15-trioxatetracyclo[11.2.1.0$^{2,6}$.0$^{8,10}$]hexadec-13(16)-ene;

ethyl 3,8-dimethyl-12-(4-methylpiperidino)-4,14-dioxo-5,9,15-trioxatetracyclo[11.2.1.0$^{2,6}$.0$^{8,10}$]hexadec-13(16)-en-11-yl carbonate;

11-hydroxy-12-isobutylsulphanyl-3-isobutylsulphanylmethyl-8-methyl-5,9,15-trioxatetracyclo[11.2.1.0$^{2,6}$.0$^{8,10}$]hexadec-13(16)-ene-4,14-dione;

11-hydroxy-12-isobutylsulphanyl-3,8-dimethyl-5,9,15-trioxatetracyclo[11.2.1.0$^{2,6}$.0$^{8,10}$]hexadec-13(16)-ene-4,14-dione;

12-(dimethylamino)-3,8-dimethyl-4,14-dioxo-5,9,15-trioxatetracyclo[11.2.1.0$^{2,6}$.0$^{8,10}$]hexadec-13(16)-en-11-yl benzoate;

12-(dimethylamino)-3,8-dimethyl-4,14-dioxo-5,9,15-trioxatetracyclo[11.2.1.0$^{2,6}$.0$^{8,10}$]hexadec-13(16)-en-11-yl acetate 12-(dimethylamino)-3,8-dimethyl-4,14-dioxo-5,9,15-trioxatetracyclo[11.2.1.0$^{2,6}$.0$^{8,10}$]hexadec-13(16)-en-11-yl cyclohexanecarboxylate;

12-(dimethylamino)-3,8-dimethyl-4,14-dioxo-5,9,15-trioxatetracyclo[11.2.1.0$^{2,6}$.0$^{8,10}$]hexadec-13(16)-en-11-yl 4-fluorobenzoate;

12-(dimethylamino)-3,8-dimethyl-4,14-dioxo-5,9,15-trioxatetracyclo[11.2.1.0$^{2,6}$.0$^{8,10}$]hexadec-13(16)-en-11-yl heptanoate;

12-(dimethylamino)-3,8-dimethyl-4,14-dioxo-5,9,15-trioxatetracyclo[11.2.1.0$^{2,6}$.0$^{8,10}$]hexadec-13(16)-en-11-yl 4-(trifluoromethyl)benzoate;

12-(dimethylamino)-3,8-dimethyl-4,14-dioxo-5,9,15-trioxatetracyclo[11.2.1.0$^{2,6}$.0$^{8,10}$]hexadec-13(16)-en-11-yl 2-thiophenecarboxylate;

12-(dimethylamino)-3,8-dimethyl-4,14-dioxo-5,9,15-trioxatetracyclo[11.2.1.0$^{2,6}$.0$^{8,10}$]hexadec-13(16)-en-11-yl 3,3-dimethylbutanoate;

12-(dimethylamino)-3,8-dimethyl-4,14-dioxo-5,9,15-trioxatetracyclo[11.2.1.0$^{2,6}$.0$^{8,10}$]hexadec-13(16)-en-11-yl 1-benzothiophene-2-carboxylate;

12-(dimethylamino)-3,8-dimethyl-4,14-dioxo-5,9,15-trioxatetracyclo[11.2.1.0$^{2,6}$.0$^{8,10}$]hexadec-13(16)-en-11-yl 2-furoate;

12-(dimethylamino)-3,8-dimethyl-4,14-dioxo-5,9,15-trioxatetracyclo[11.2.1.0$^{2,6}$.0$^{8,10}$]hexadec-13(16)-en-11-yl 5-nitro-2-furoate;

12-(dimethylamino)-3,8-dimethyl-4,14-dioxo-5,9,15-trioxatetracyclo[11.2.1.0$^{2,6}$.0$^{8,10}$]hexadec-13(16)-en-11-yl 2-thienylacetate;

12-(dimethylamino)-3,8-dimethyl-4,14-dioxo-5,9,15-trioxatetracyclo[11.2.1.0$^{2,6}$.0$^{8,10}$]hexadec-13(16)-en-11-yl phenoxyacetate;

8-(dimethylamino)-3,10a-dimethyl-2,6-dioxodecahydro-4,7-methenofuro[3,2-c]oxireno[f]oxacycloundecin-9-yl 4-tert-butylphenylcarbamate;

8-(dimethylamino)-3,10a-dimethyl-2,6-dioxodecahydro-4,7-methenofuro[3,2-c]oxireno[f]oxacycloundecin-9-yl thien-2-ylcarbamate;

8-(dimethylamino)-3,10a-dimethyl-2,6-dioxodecahydro-4,7-methenofuro[3,2-c]oxireno[f]oxacycloundecin-9-yl 2-methoxyphenylcarbamate;

8-(dimethylamino)-3,10a-dimethyl-2,6-dioxodecahydro-4,7-metheno-furo[3,2-c]oxireno [f]oxacycloundecin-9-yl 2(methylthio)phenylcarbamate;

8-(dimethylamino)-3,10a-dimethyl-2,6-dioxodecahydro-4,7-methenofuro[3,2-c]oxireno[f]oxacycloundecin-9-yl 2-ethoxyphenylcarbamate;

8-(dimethylamino)-3,10a-dimethyl-2,6-dioxodecahydro-4,7-methenofuro[3,2-c]oxireno[f]oxacycloundecin-9-yl thien-3-ylcarbamate;

8-(dimethylamino)-3,10a-dimethyl-2,6-dioxodecahydro-4,7-methenofuro[3,2-c]oxireno[f]oxacycloundecin-9-yl 1-benzothien-3-ylcarbamate;

8-(dimethylamino)-3,10a-dimethyl-2,6-dioxodecahydro-4,7-metheno-furo[3,2-c]oxireno[f]oxacycloundecin-9-yl N-(ter-butoxycarbonyl)glycinate;

8-(dimethylamino)-3,10a-dimethyl-2,6-dioxodecahydro-4,7-methenofuro [3,2-c]oxireno[f]oxacycloundecin-9-yl thien-3-ylacetate;

8-(dimethylamino)-3,10a-dimethyl-2,6-dioxodecahydro-4,7-methenofuro[3,2-c]oxireno[f]oxacycloundecin-9-yl 1-benzothien-3-ylacetate;

8-(dimethylamino)-3,10a-dimethyl-2,6-dioxodecahydro-4,7-methenofuro[3,2-c]oxireno[f]oxacycloundecin-9-yl thiophene-3-carboxylate;

8-(dimethylamino)-3,10a-dimethyl-2,6-dioxodecahydro-4,7-methenofuro[3,2-c]oxireno[f]oxacycloundecin-9-yl 5-phenylthien-2-ylcarbamate;

8-(dimethylamino)-3,10a-dimethyl-2,6-dioxodecahydro-4,7-methenofuro[3,2-c]oxireno[f]oxacycloundecin-9-yl 1-adamantylcarbamate;

8-(dimethylamino)-3,10a-dimethyl-2,6-dioxodecahydro-4,7-methenofuro[3,2-c]oxireno[f]oxacycloundecin-9-yl 2-naphthylcarbamate;

8-(dimethylamino)-3,10a-dimethyl-2,6-dioxodecahydro-4,7-metheno-furo[3,2-c]oxireno[f]oxacycloundecin-9-yl 2-tert-butyl-6-methylphenylcarbamate;

8-(dimethylamino)-3,10a-dimethyl-2,6-dioxodecahydro-4,7-metheno-furo[3,2-c]oxireno[f]oxacycloundecin-9-yl 2,5-dimethoxyphenylcarbamate;

as well as their salts.

The invention quite particularly relates to the following compounds:

12-dimethylamino-11-hydroxy-3,8-dimethyl-5,9,15-trioxatetracyclo[11.2.1.0$^{2,6}$.0$^{8,10}$]hexadec-13(16)-ene-4,14-dione;

11-(tert-butyldimethylsiloxy)-12-dimethylamino-3,8-dimethyl-5,9,15-trioxatetracyclo[11.2.1.0$^{2,6}$.0$^{8,10}$]hexadec-13(16)-ene-4,14-dione;

12-(dimethylamino)-3,8-dimethyl-4,14-dioxo-5,9,15-trioxatetracyclo[11.2.1.0$^{2,6}$.0$^{8,10}$]hexadec-13(16)-en-11-yl benzoate;

12-(dimethylamino)-3,8-dimethyl-4,14-dioxo-5,9,15-trioxatetracyclo[11.2.1.0$^{2,6}$.0$^{8,10}$]hexadec-13(16)-en-11-yl cyclohexanecarboxylate;

12-(dimethylamino)-3,8-dimethyl-4,14-dioxo-5,9,15-trioxatetracyclo[11.2.1.0$^{2,6}$.0$^{8,10}$]hexadec-13(16)-en-11-yl 4-fluorobenzoate;

12-(dimethylamino)-3,8-dimethyl-4,14-dioxo-5,9,15-trioxatetracyclo[11.2.1.0$^{2,6}$.0$^{8,10}$]hexadec-13(16)-en-11-yl 2-thiophenecarboxylate;

12-(dimethylamino)-3,8-dimethyl-4,14-dioxo-5,9,15-trioxatetracyclo[11.2.1.0$^{2,6}$.0$^{8,10}$]hexadec-13(16)-en-11-yl 3,3-dimethylbutanoate;

12-(dimethylamino)-3,8-dimethyl-4,14-dioxo-5,9,15-trioxatetracyclo[11.2.1.0$^{2,6}$.0$^{8,10}$]hexadec-13(16)-en-1-yl 1-benzothiophene-2-carboxylate;

8-(dimethylamino)-3,10a-dimethyl-2,6-dioxodecahydro-4,7-methenofuro[3,2-c]oxireno[f]oxacycloundecin-9-yl 4-tert-butylphenylcarbamate;

8-(dimethylamino)-3,10a-dimethyl-2,6-dioxodecahydro-4,7-methenofuro[3,2-c]oxireno[f]oxacycloundecin-9-yl 2-ethoxyphenylcarbamate;

as well as their salts.

As regards the salts of compounds of general formula (I), the maleates, fumarates, methanesulphonates and hydrochlorides of compounds of general formula (I) are preferred, and in particular those described in the examples, namely:

11-hydroxy-3,8-dimethyl-4,14-dioxo-5,9,15-trioxatetracyclo[11.2.1.0$^{2,6}$.0$^{8,10}$]hexadec-13(16)-ene-12-yl(dimethyl)ammonium maleate;

11-hydroxy-3,8-dimethyl-4,14-dioxo-5,9,15-trioxatetracyclo[11.2.1.0$^{2,6}$.0$^{8,10}$]hexadec-13(16)-ene-12-yl(dimethyl)ammonium fumarate;

11-hydroxy-3,8-dimethyl-4,14-dioxo-5,9,15-trioxatetracyclo[11.2.1.0$^{2,6}$.0$^{8,10}$]hexadec-13(16)-ene-12-yl(dimethyl)ammonium methanesulphonate;

11-{[tert-butyl(dimethyl)silyl]oxy}-12-(dimethylamino)-3,8-dimethyl-5,9,15-trioxatetracyclo[11.2.1.0$^{2,6}$.0$^{8,10}$] hexadec-13(16)-ene-4,14-dione hydrochloride 12-(dimethylamino)-3,8-dimethyl-4,14-dioxo-5,9,15-trioxatetracyclo[11.2.1.0$^{2,6}$.0$^{8,10}$]hexadec-13(16)-en-11-yl 2-thiophenecarboxylate hydrochloride.

A subject of the invention is also the compounds of general formula (I)':

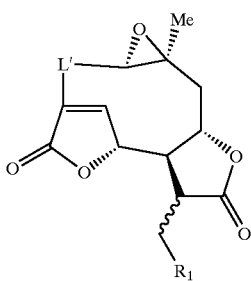

(I)' corresponding to general sub-formulae (I)'$_1$ and (I)'$_2$:

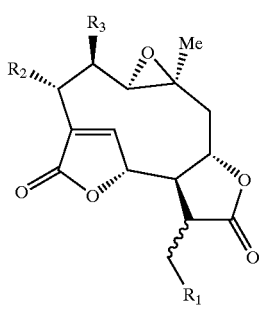

(I)'$_1$

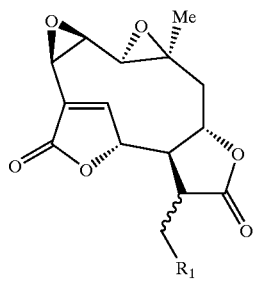

(I)'$_2$ in which $R_1$ represents a hydrogen atom or an $SR_4$ or $NR_4R_5$ radical;

$R_2$ represents $SR_6$ or $NR_6R_7$;

$R_3$ represents OH, O(CO)$R_{14}$, O(CO)O$R_{14}$, or OSi$R_{15}R_{16}R_{17}$;

$R_4$, and $R_6$ represent, independently, an alkyl radical, a cycloalkyl, cycloalkylalkyl, hydroxyalkyl radical or also one of the aryl or aralkyl radicals optionally substituted on their aryl group by one or more radicals chosen from the alkyl, hydroxy or alkoxy radicals, $R_5$ and $R_7$ represent, independently, a hydrogen atom, an alkyl radical, a cycloalkyl, cycloalkylalkyl, hydroxyalkyl radical or also one of the aryl or aralkyl radicals optionally substituted on their aryl group by one or more radicals chosen from the alkyl, hydroxy or alkoxy radicals, $R_4$ and $R_5$ being able to form together with the nitrogen atom which carries them a heterocycle with 5 to 7 members, the additional members being chosen from the —$CR_8R_9$—, —$NR_{10}$—, —O— and —S— radicals, it being understood however that there can only be one member chosen from —O— or —S— in said heterocycle, and $R_6$ and $R_7$ being able to form together with the nitrogen atom which carries them a heterocycle with 5 to 7 members, the additional members being chosen from the —$CR_{11}R_{12}$—, —$NR_{13}$—, —O— and —S— radicals, it being understood however that there can only be one member chosen from —O— or —S— in said heterocycle, $R_8$, $R_{10}$, $R_{11}$ and $R_{13}$ represent, independently each time they are involved, a hydrogen atom or an alkyl, alkoxycarbonyl or aralkyl radical, $R_9$ and $R_{12}$ representing, independently each time they are involved, a hydrogen atom or each of $R_9$ and $R_{12}$ being able to form respectively with $R_8$ and $R_{11}$ an —O—(CH$_2$)$_2$—O— radical attached on either side to the carbon atom which carries them, such a radical only being present however once at most per $NR_4R_5$ or $NR_6R_7$ radical, represent, independently each time they are involved, a hydrogen atom or an alkyl radical;

$R_{14}$ represents an alkyl or cycloalkyl radical or one of the aryl, heteroaryl, aralkyl or heteroaralkyl radicals optionally substituted on their aryl or heteroaryl group by one or more radicals chosen from a halogen atom and the alkyl, haloalkyl, nitro, hydroxy or alkoxy radicals;

$R_{15}$, $R_{16}$ and $R_{17}$ represent, independently, an alkyl radical or a phenyl radical;

it being understood however that when the compounds correspond to general sub-formula (I)'$_2$, then $R_1$ does not represent a hydrogen atom;

or the salts of the latter.

A subject of the invention is also the compounds of general formula (I)":

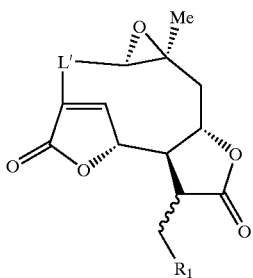

(I)″ corresponding to the general sub-formulae (I)″₁ and (I)″₂:

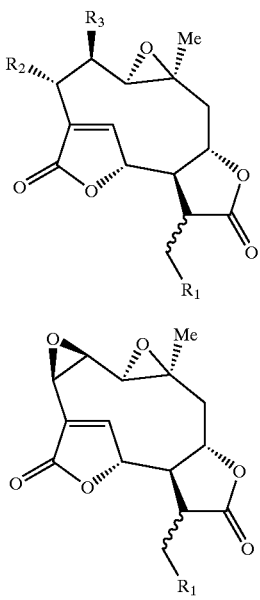

in which

R₁ represents a hydrogen atom or an SR₄ or NR₄R₅ radical;

R₂ represents SR₆ or NR₆R₇;

R₃ represents OH, O(CO)R₁₄, O(CO)OR₁₄, or OSiR₁₅R₁₆R₁₇;

R₄, R₅, R₆ and R₇ represent, independently, a hydrogen atom, an alkyl radical, a cycloalkyl, cycloalkylalkyl, hydroxyalkyl radical or also one of the aryl or aralkyl radicals optionally substituted on their aryl group by one or more radicals chosen from the alkyl, hydroxy or alkoxy radicals, R₄ and R₅ can form together with the nitrogen atom which carries them a heterocycle with 5 to 7 members, the additional members being chosen from the —CR₈R₉—, —NR₁₀—, —O— and —S— radicals, it being understood however that only one member chosen from —O— or —S— can be found in said heterocycle, and R₆ and R₇ can form together with the nitrogen atom which carries them a heterocycle with 5 to 7 members, the additional members being chosen from the —CR₁₁R₁₂—, —NR₁₃—, —O— and —S— radicals, it being understood however that only one member chosen from —O— or —S— can be found in said heterocycle, R₈, R₁₀, R₁₁ and R₁₃ represent, independently each time they are involved, a hydrogen atom or an alkyl, alkoxycarbonyl or aralkyl radical, R₉ and R₁₂ representing, independently each time they are involved, a hydrogen atom or each of R₉ and R₁₂ can form with R₈ and R₁₁ respectively an —O—(CH₂)₂—O— radical attached on either side to the carbon atom which carries it, such radical however only being present at most once per NR₄R₅ or NR₆R₇ radical, represent, independently each time they are involved, a hydrogen atom or an alkyl radical;

R₁₄, R₁₅, R₁₆ and R₁₇ represent, independently, a hydrogen atom, an alkyl radical or one of the aryl or aralkyl radicals optionally substituted on their aryl group by one or more radicals chosen from the alkyl, hydroxy or alkoxy radicals;

it being understood however that when the compounds correspond to the general sub-formula (I)″₂, then R₁ does not represent a hydrogen atom;

or the salts of the latter.

The compounds of the present invention can inhibit abnormal cell proliferation in a patient, for example a mammal such as man, by administration to this patient of a therapeutically effective quantity of a compound of general formula (I), (I)' or (I)" or of a pharmaceutically acceptable salt of such a compound.

The compounds of general formula (I), (I)' or (I)" have an anti-tumoral activity. They can be used for the treatment of tumors in a patient by administration to said patient of a therapeutically effective quantity of a compound of general formula (I), (I)' or (I)" or of a pharmaceutically acceptable salt of such a compound. Examples of tumors or cancers include cancers of the oesophagus, stomach, intestines, rectum, buccal cavity, pharynx, larynx, lung, colon, breast, cervix uteri, corpus endometrium, ovaries, prostate, testicles, bladder, kidneys, liver, pancreas, bone, connective tissues, skin, for example melanomas, eyes, brain and central nervous system, as well as cancer of the thyroid, leukemia, Hodgkin's disease, lymphomas other than those of Hodgkin's disease, multiple myelomas and others.

They can also be used for the treatment of parasitic infections by inhibition of the hemoflagellates (for example in trypanosomia or leishmania infections) or by inhibition of the plasmodia (such as for example in malaria), but also the treatment of viral infections and diseases.

These properties make the compounds of the invention suitable for pharmaceutical use. A subject of the invention is therefore also, as medicaments, the compounds of general formula (I), (I)' or (I)" described previously or their pharmaceutically acceptable salts. It also relates to pharmaceutical compositions containing these compounds or their pharmaceutically acceptable salts. A further subject of the invention is the use of these compounds or their pharmaceutically acceptable salts in order to produce medicaments intended to inhibit DNA polymerases, and in particular to treat diseases due to abnormal cell proliferation (in particular cancer or atherosclerosis, benign hyperplasia of the prostate and fibroses), as well as viral diseases and parasitic diseases, in particular those caused by protozoans (for example malaria) or protists (for example diseases caused by amoebae). Finally, the invention relates to the use of the compounds of general formula (I), (I)' or (I)" described previously or their pharmaceutically acceptable salts for preparing a medicament intended to treat diseases of bacterial origin.

By pharmaceutically acceptable salt is meant in particular addition salts of inorganic acids such as hydrochloride, hydrobromide, hydroiodide, sulphate, phosphate, diphosphate and nitrate or organic acids such as acetate, maleate, fumarate, tartrate, succinate, citrate, lactate, methanesulphonate, p-toluenesulphonate, pamoate and stearate. The salts formed from bases such as sodium or potassium hydroxide also fall within the scope of the present invention, when they can be used. For other examples of pharmaceutically acceptable salts, reference can be made to "Salt selection for basic drugs", *Int. J. Pharm.* (1986), 33, 201–217.

The pharmaceutical compositions containing a compound of the invention can be in solid form such as, for example, powders, pills, granules, tablets, liposomes, gelatin capsules or suppositories. The pills, tablets or gelatin capsules can be coated with a substance capable of protecting the composition from the action of the gastric acid or the enzymes in the subject's stomach for a sufficient period of time to allow this composition to pass undigested into the subject's small intestine. The compound can also be administered locally, for example at the precise location of a tumor. The compound can also be administered according to a sustained release process (for example using a sustained release composition or a perfusion pump). Appropriate solid supports can be, for example, calcium phosphate, magnesium stearate, magnesium carbonate, talc, sugars, lactose, dextrin, starch, gelatin, cellulose, methyl cellulose, sodium carboxymethyl cellulose, polyvinylpyrrolidine and wax.

The pharmaceutical compositions containing a compound of the invention can also be presented in liquid form such as, for example, solutions, emulsions, suspensions or a sustained release formulation. Appropriate liquid supports can be, for example, water, organic solvents such as glycerol or glycols such as polyethylene glycol, as well as their mixtures, in varying proportions, in water.

The administration of a medicament according to the invention can be carried out by topical, oral, parenteral route, by intramuscular injection, etc.

The dose of a compound according to the present invention, to be provided for the treatment of the diseases or disorders indicated above, varies according to the method of administration, the age and the body weight of the subject to be treated as well as the latter's state, and the final decision is made by the attending doctor or veterinary surgeon. Such a quantity determined by the attending doctor or veterinary surgeon is here referred to as "therapeutically effective quantity".

The same preferences as those indicated previously for the compounds of general formula (I) are applicable mutatis mutandis to the compounds of general formula (I)' or (I)", to the medicaments of general formula (I), (1)' or (I)", to the pharmaceutical compositions containing a compound of general formula (I), (I)' or (I)" and to the uses of a compound of general formula (I), (I)' or (I)" for preparing medicaments.

According to the invention, the compounds of general formula (I), (I)' or (I)" can be prepared by the processes described hereafter.

Preparation of Compounds of General Formula (I), (I)' or (I)" and their Salts

Preparation of Compounds of General Sub-formula $(I)_1$:

Case 1: $R_1$=H:

The preparation of this type of compound is summarized in Diagram 1 hereafter. The dihydromikanolide by adding a nucleophile such as a primary or secondary amine $HNR_6R_7$, or also a thiol $R_6SH$ in the presence of a base, in an inert solvent such as tetrahydrofuran or acetone, at a temperature preferably comprised between 0° C. and 50° C., and more preferentially at ambient temperature.

In the case where $R_3$ is not OH, the intermediate obtained is treated with one of the reagents of general formula $R_{14}$(CO)-Hal (or an equivalent reagent such as for example the anhydride $(R_{14}(CO))_2O$), $R_{18}O(CO)$-Hal, Hal-Si$R_{15}R_{16}R_{17}$ (Hal representing a halogen atom) or $R_{18}$—NCO in order to obtain the desired final compound. Generally, this reaction is carried out in an aprotic solvent such as dichloromethane, trichloroethane, acetonitrile, tetrahydrofuran or toluene, at a temperature preferably comprised between 0° C. and 110° C. and optionally in the presence of a base such as triethylamine or 4-dimethylaminopyridine. These types of reaction are well known to a person skilled in the art (who can in particular usefully consult the following reference publication: Greene et al., *"Protective groups in Organic Synthesis"*, 2nd edition, Wiley, New-York, 1991) owing to their frequent use for protecting an alcohol or amine function. For example, as regards the silylation reaction, this is generally carried out by treatment of an alcoholic compound with a silyl chloride in the presence of a base, in an aprotic solvent at a temperature comprised between 0° C. and 50° C.

Diagram 1

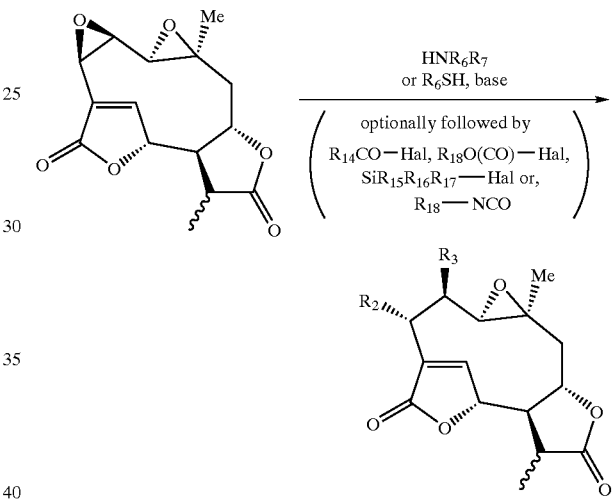

An additional method for obtaining compounds with $R_3$=OCOR$_{14}$ consists of treating the intermediate alcohol with the acid $R_{14}$—COOH in the presence of a base, such as for example dimethylaminopyridine, and a coupling agent, such as for example 1-(3-dimethylaminopropyl)-3-ethylcarbodiimide hydrochloride (EDC.HCl).

Case 2: $R_1$=$R_2$≠H :

The compounds of formula $(I)_1$ in which $R_1$=$R_2$≠H and $R_3$ represents a hydroxyl group can be prepared from mikanolide by adding a nucleophilic such as a primary or secondary amine $HNR_4R_5$, or also a thiol $R_4SH$ in the presence of a base, in an inert solvent such as tetrahydrofuran or acetone, at a temperature preferably comprised between 0° C. and 50° C., and more preferentially at ambient temperature.

In the case where $R_3$ is not OH, a second reaction is carried out using a compound of general formula $R_{14}$(CO)-Hal (or an equivalent reagent such as for example $(R_{14}(CO))_2O$), $R_{18}O(CO)$-Hal or Hal-SiR$_{15}R_{16}R_{17}$ anhydride (Hal representing a halogen atom) or $R_{18}$—NCO in order to obtain the desired final compound. This reaction can be carried out in a manner analogous to that disclosed in CASE 1.

Diagram 2

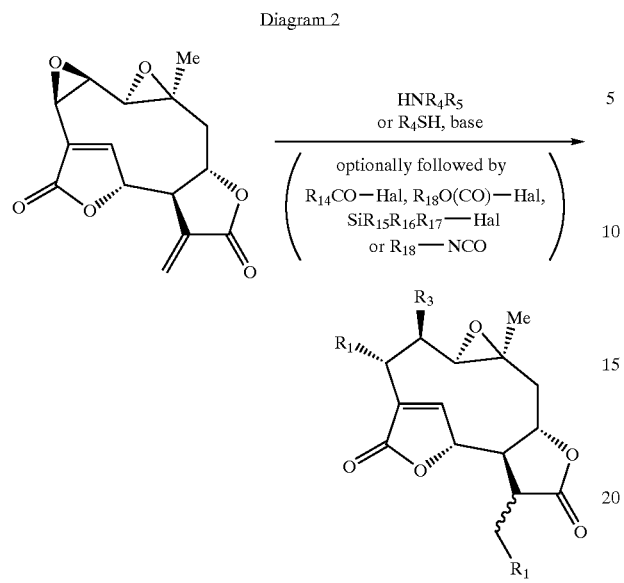

Diagram 4

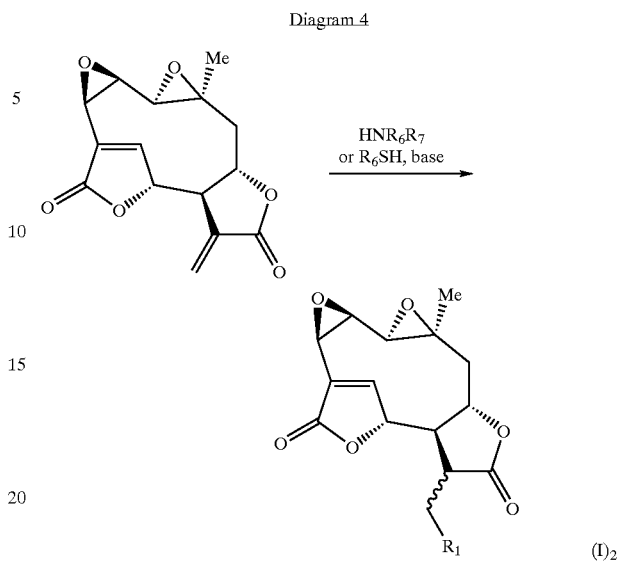

An additional method for obtaining compounds with $R_3=OCOR_{14}$ consists of treating the intermediate alcohol with the acid $R_{14}$—COOH in the presence of a base, such as for example dimethylaminopyridine, and of a coupling agent, such as for example 1-(3-dimethylaminopropyl)-3-ethylcarbodiimide hydrochloride (EDC.HCl).

Case 3: $R_1 \neq H$ and $R_1 \neq R_2$:

In this case, the compound of general formula $(I)_2$ is subjected to the same reactions as in CASE 1 in order to produce the desired final compound in which $R_1 \neq R_2$.

Diagram 3

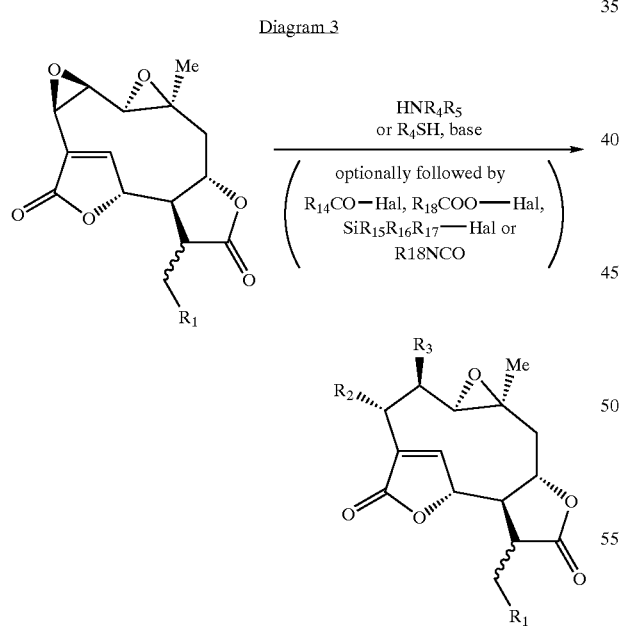

Preparation of Compounds of General Sub-formula $(I)_2$:

The compounds of sub-formula $(I)_2$ can be prepared, Diagram 4, from mikanolide by adding a nucleophile such as a primary or secondary amine $HNR_6R_7$, or also a thiol $R_6SH$ in the presence of a base, in an inert solvent such as tetrahydrofuran or acetone, at a temperature preferably comprised between 0° C. and 50° C., and more preferentially at ambient temperature.

Salts of Compounds of General Formula (I):

Certain compounds of the invention can be prepared in the form of pharmaceutically acceptable salts according to the usual methods. As regards these salts, a person skilled in the art can usefully consult the article by Gould et al., "Salt selection for basic drugs", Int. J. Pharm. (1 986), 33, 201–217.

Unless otherwise specified, all the technical and scientific terms used here have the same meaning as that usually understood by an ordinary specialist in the field to which this invention belongs. Similarly, all the publications, patent applications, all the patents and all other references mentioned here are incorporated by way of reference.

The following examples are presented in order to illustrate the above procedures and should in no event be considered as a limit to the scope of the invention.

EXAMPLES

The nomenclature used for the examples in principle conforms with the IUPAC standards. It was determined using the ACD/Name® software (version 4.53) for examples 1 to 36 and using the ACD/Name® software (version 5.00) for examples 37 to 52.

The numbering indicated in the figure below is used for examples 1 to 36 as regards the positions of the substituents —CH$_2$—R$_1$, R$_2$ and R$_3$ on the polycycles of general sub-formulae $(I)_1$ and $(I)_2$:

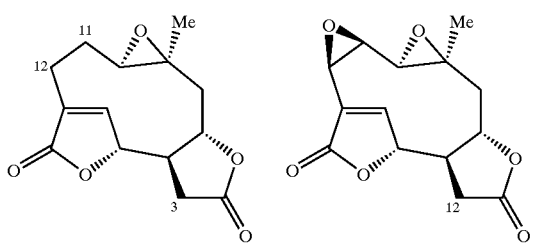

Example 1

12-diisopropylaminomethyl-7-methyl-3.6,10,15-tetraoxapentacyclo[12.2.1.0$^{2,4}$.0$^{5,7}$.0$^{9,13}$]heptadec-1(17)-ene-11,16-dione Diisopropylamine (500 µmol; 70 µl) is added to a solution of mikanolide (100 µmol; 29 mg) in acetone (1 ml). The reaction mass is stirred for 30 minutes at ambient temperature then the solvent is eliminated by evaporation under reduced pressure. The residue is taken up in ether, filtered and dried under vacuum. 10 mg of product is obtained in the form of a white powder.

NMR-$^1$H (DMSO): 0.90–1.30 (m, 15H); 1.85 (m, 2H); 2.15 (t, 2H); 3.15–3.50 (m, 4H); 3.95 (s, 1H); 4.75 (m, 1H); 5.50 (s, 1H); 6.00 (s, 1H); 6.25 (s, 1H); 7.60 (s, 1H).

Example 2

12-dimethylamino-3-dimethylaminomethyl-11-hydroxy-8-methyl-5,9,15-trioxatetracyclo[11.2.1.0$^{2,6}$.0$^{8,10}$]hexadec-13(16)-ene-4,14-dione A solution of dimethylamine (160 μmol; 80 μl; 2M in THF) is added to a solution of mikanolide (30 μmol; 9 mg) in acetone (0.3 ml). The reaction mass is stirred for 30 minutes at ambient temperature then concentrated under reduced pressure. The residue is taken up in ether, filtered and dried under vacuum. 6 mg of expected compound is obtained in the form of a white powder.

NMR-$^1$H (DMSO): 1.11 (s, 3H); 1.94–1.97 (m, 2H); 2.20 (s, 6H); 2.47 (s, 6H); 2.67 (m, 2H); 2.85 (t, 1H); 3.07 (d, 1H); 3.15 (m, 1H); 3.52 (d, 1H); 3.63 (m, 1H); 4.62 (m, 1H); 5.36 (s, 1H); 5.47 (s, 1H); 8.00 (s, 1H). NMR-$^{13}$C (DMSO): 20.68; 42.85; 43.37; 44.71; 45.92; 49.95; 57.84; 58.24; 61.61; 62.97; 67.94; 77.09; 80.67; 131.46; 151.01; 172.03; 174.98.

Example 3

12-benzyl(methyl)amino-3-benzyl(methyl)aminomethyl-11-hydroxy-8-methyl-5,9,15-trioxatetracyclo[11.2.1.0$^{2,6}$.0$^{8,10}$]hexadec-13(16)-ene-4,14-dione This compound is obtained by a procedure similar to that described for the synthesis of the compound of Example 2. The expected product is obtained in the form of a white powder.

NMR-$^1$H (DMSO): 1.12 (s, 3H); 1.96 (m, 2H); 2.10 (m, 1H); 2.15 (s, 3H); 2.47 (m, 2H); 2.83 (d, 2H); 2.89 (d, 1H); 3.22 (d, 1H); 3.26 (m, 1H); 3.58 (dd, 2H); 3.69 (m, 1H); 3.89 (d, 1H); 3.93 (s, 2H); 4.73 (m, 1H); 5.47 (d, 1H); 5.52 (s, 1H); 7.23–7.40 (m, 10H); 8.10 (s, 1H). NMR-$^{13}$C (DMSO): 20.65; 39.08; 40.54; 42.09; 43.09; 43.52; 50.18; 56.57; 57.85; 60.17; 61.14; 62.21; 62.33; 68.37; 77.22; 81.01; 126.07; 128.30; 131.48; 138.88; 139.67; 150.35; 172.16; 175.18.

Example 4

11-hydroxy-8-methyl-12-morpholino-3-morpholinomethyl-5,9,15-trioxatetracyclo[11.2.1.0$^{2,6}$.0$^{8,10}$]hexadec-13(16)-ene-4,14-dione This compound is obtained by a procedure similar to that described for the synthesis of the compound of Example 2. The expected product is obtained in the form of a white powder.

NMR-$^1$H (DMSO): 1.13 (s, 3H); 1.85–2.10 (m, 2H); 2.36 (m, 2H); 2.40 (m, 2H); 2.74 (m, 4H); 2.88 (t, 1H); 2.95 (m, 2H); 3.10 (d, 1H); 3.24 (m, 1H); 3.50–3.70 (m, 10H); 4.64 (m, 1H); 5.49 (s, 1H); 5.50 (d, 1H); 8.01 (s, 1H).

Example 5

12-dimethylamino-11-hydroxy-3,8-dimethyl-5,9,15-trioxatetracyclo[11.2.1.0$^{2,6}$.0$^{8,10}$]hexadec-13(16)-ene-4,14-dione A solution of dimethylamine (500 μmol, 250 μl, 2M in THF) is added to a solution of dihydromikanolide (100 μmol, 29 mg) in acetone (1 ml). The reaction mass is stirred for 2 hours at ambient temperature then the solvent is eliminated by evaporation under reduced pressure. The residue is taken up in ether, filtered and dried under vacuum. 25 mg of product is obtained in the form of a white powder.

NMR-$^1$H (DMSO): 1.10 (s, 3H); 1.25 (d, 3H), 1.90 (dd, 1H); 1.99 (t, 1H); 2.49 (s, 6H); 2.58 (t, 1H); 2.94 (m, 1H); 3.06 (d, 1H); 3.51 (m, 1H); 3.63 (m, 1H); 4.62 (m, 1H); 5.34 (s, 1H); 5.37 (d, 1H); 8.00 (s, 1H).

Example 6

11-hydroxy-3,8-dimethyl-4,14-dioxo-5,9,15-trioxatetracyclo[11.2.1.0$^{2,6}$.0$^{8,10}$]hexadec-13(16)-ene-12-yl(dimethyl)ammonium maleate A solution of maleic acid (0.1 mmol; 11.6 mg) in acetone (0.5 ml) is added to a solution of the compound of Example 5 (0.1 mmol; 34 mg) in acetone (0.5 ml). The precipitate is filtered, washed with acetone and dried under reduced pressure. 24 mg of the expected product is obtained in the form of a white powder. Melting point: 178.5° C.

NMR-$^1$H (DMSO): 1.09 (s, 3H); 1.28 (d, 3H); 1.94 (dd, 1H); 2.05 (m, 1H); 2.63 (t, 1H); 2.70–3.70 (m, 9H); 3.79 (t, 1H); 4.38 (s, 1H); 4.68 (m, 1H); 5.45 (s, 1H); 6.07 (s, 2H); 8.31 (s, 1H).

Example 7

11-hydroxy-3,8-dimethyl-4,14-dioxo-5,9,15-trioxatetracyclo[11.2.1.0$^{2,6}$.0$^{8,10}$]hexadec-13(16)-ene-12-yl(dimethyl)ammonium fumarate A solution of fumaric acid (0.1 mmol; 11.6 mg) in acetone (3 ml) is added to a solution of the compound of Example 5 (0.1 mmol; 34 mg) in acetone (0.5 ml). The precipitate is filtered, washed with acetone and dried under reduced pressure. 15 mg of the expected product is obtained in the form of a white powder. Melting point: 159° C.

NMR-$^1$H (DMSO): 1.11 (s, 3H); 1.25 (d, 3H); 1.92 (dd, 1H); 2.02 (m, 1H); 2.58 (t, 1H); 2.80–4.00 (m, 11H); 4.64 (m, 1H); 5.34 (s, 1H); 6.61 (s, 2H); 8.01 (s, 1H).

Example 8

11-hydroxy-3,8-dimethyl-4,14-dioxo-5,9,15-trioxatetracyclo[11.2.1.0$^{2,6}$.0$^{8,10}$]hexadec-13(16)-ene-12-yl(dimethyl)ammonium methanesulphonate A solution of methanesulphonic acid (0.1 mmol; 1 ml; 0.1N in acetone) is added to a solution of the compound of Example 5 (0.1 mmol; 34 mg) in acetone (2 ml). The precipitate is filtered, washed with acetone and dried under reduced pressure. 24 mg of the expected product is obtained in the form of a white powder. Melting point: 220° C.

NMR-$^1$H (DMSO): 1.09 (s, 3H); 1.29 (d, 3H); 1.97 (dd, 1H); 2.07 (m, 1H); 2.30 (s, 3H); 2.65 (t, 1H); 2.80–3.15 (m, 7H); 3.28 (d, 1H); 3.85 (t, 1H); 4.66–4.72 (m, 2H); 5.49 (s, 1H); 6.94 (s, 1H); 8.44 (s, 1H); 10.04 (s, 1H).

Example 9

11-hydroxy-3,8-dimethyl-12-(4-methylpiperidino)-5,9,15-trioxatetracyclo[11.2.1.0$^{2,6}$.0$^{8,10}$]hexadec-13(16)-ene-4,14-dione This compound is obtained by a procedure similar to that described for the synthesis of the compound of Example 5. The expected product is obtained in the form of a white powder. Melting point: 210° C.

NMR-$^1$H (DMSO): 0.80–3.50 (m, 23H); 3.60–3.75 (m, 2H); 4.62 (m, 1H); 5.32 (s, 2H); 8.01 (s, 1H).

Example 10

11-hydroxy-3,8-dimethyl-12-pyrrolidino-5,9,15-trioxatetracyclo[11.2.1.0$^{2,6}$.0$^{8,10}$]hexadec-13(16)-ene-4,14-dione This compound is obtained by a procedure similar to that described for the synthesis of the compound of Example 5. The expected product is obtained in the form of a white powder.

NMR-$^1$H (DMSO): 1.12 (s, 3H); 1.25 (d, 3H); 1.69 (m, 4H); 1.91 (dd, 1H); 2.00 (m, 1H); 2.60 (t, 1H); 2.80 (m, 4H); 2.95 (m, 1H); 3.02 (d, 1H); 3.45 (s, 1H); 3.63 (m, 1H); 4.61 (m, 1H); 5.34 (s, 1H); 5.42 (d, 1H); 7.97 (s, 1H).

Example 11 ethyl 1-[11-hydroxy-3,8-dimethyl-4,14-dioxo-5,9,15-trioxatetracyclo[11.2.1.0$^{2,6}$]hexadec-13(16)-ene-12-yl]-4-piperidinecarboxylate This compound is obtained by a procedure similar to that described for the synthesis of the compound of Example 5. The expected product is obtained in the form of a white powder.

NMR-$^1$H (DMSO): 1.00–4.00 (m, 25H); 4.04 (q, 2H); 4.64 (m, 1H); 5.35 (s, 1H); 5.48 (d, 1H); 8.07 (s,1H).

Example 12

12-(4-benzylpiperidino)-11-hydroxy-3,8-dimethyl-5,9,15-trioxatetracyclo[11.2.1.0$^{2,6}$.0$^{8,10}$]hexadec-13(16)-ene-4,14-dione This compound is obtained by a procedure similar to that described for the synthesis of the compound of Example 5. The expected product is obtained in the form of a white powder.

NMR-$^1$H (DMSO): 1.00–1.80 (m, 12H); 1.85–2.10 (m, 2H); 2.35–4.00 (m, 6H); 4.63 (m, 1H); 5.33 (m, 2H); 7.00–7.20 (m, 5H); 8.03 (s, 1H).

Example 13

11-hydroxy-3,8-dimethyl-12-piperidino-5,9,15-trioxatetracyclo[11.2.1.0$^{2,6}$.0$^{8,10}$]hexadec-13(16)-ene-4,14-dione This compound is obtained by a procedure similar to that described for the synthesis of the compound of Example 5. The expected product is obtained in the form of a white powder.

NMR-$^1$H (DMSO): 1.11 (s, 3H); 1.26 (d, 3H); 1.35–1.70 (m, 6H); 1.85–2.14 (m, 2H); 2.57–3.18 (m, 7H); 3.50–3.75 (m, 2H); 4.64 (m, 1H); 5.34 (m, 2H); 8.04 (s, 1H).

Example 14

12-(1,4-dioxa-8-azaspiro[4.5]dec-8-yl)-11-hydroxy-3,8-dimethyl-5,9,15-trioxatetracyclo[11.2.1.0$^{2,6}$.0$^{8,10}$]hexadec-13(16)-ene-4,14-dione This compound is obtained by a procedure similar to that described for the synthesis of the compound of Example 5. The expected product is obtained in the form of a white powder.

NMR-$^1$H (DMSO): 1.11 (s, 3H); 1.26 (d, 3H); 1.40–1.80 (m, 6H); 1.85–2.05 (m, 2H); 2.58–4.00 (m, 17H); 4.67 (m, 1H); 5.37 (s, 1H); 5.44 (d, 1H); 8.08 (s, 1H).

Example 15

11-hydroxy-3,8-dimethyl-12-morpholino-5,9,15-trioxatetracyclo[11.2.1.0$^{2,6}$.0$^{8,10}$]hexadec-13(16)-ene-4,14-dione This compound is obtained by a procedure similar to that described for the synthesis of the compound of Example 5. The expected product is obtained in the form of a white powder.

NMR-$^1$H (DMSO): 1.10 (s, 3H); 1.25 (d, 3H); 1.89 (dd, 1H); 2.01 (m, 1H); 2.61 (t, 1H); 2.75 (m, 2H); 3.95 (m, 3H); 3.08 (d, 1H); 3.55–3.75 (m, 5H); 4.63 (1H); 5.33 (s, 1H); 5.54 (d, 1H); 8.04 (s, 1H).

Example 16

11-(tert-butyldimethylsiloxy)-12-dimethylamino-3,8-dimethyl-5,9,15-trioxatetracyclo[11.2.1.0$^{2,6}$.0$^{8,10}$]hexadec-13(16)-ene-4,14-dione Terbutyldimethylsilyl chloride (80 μmol, 12 mg) is added to a solution of the compound of Example 5 (80 μmol; 27 mg) and imidazole (160 μmol; 11 mg) in DMF (0.5 ml). The solution obtained is stirred for 20 hours then the reaction mass is poured into water. The aqueous phase is extracted twice with ethyl acetate, the organic phase is washed with water then with a solution of sodium chloride. The organic phase is dried over magnesium sulphate, filtered then evaporated. The residue is eluted on silica with a mixture of isopropyl acetate and dichloromethane (20/80). 20 mg of product is obtained in the form of a white powder.

NMR-$^1$H (DMSO): 0.04 (s, 3H); 0.07 (s, 3H); 0.89 (s, 9H); 1.14 (s, 3H); 1.25 (d, 3H); 1.90 (dd, 1H); 1.99 (dd, 1H); 2.48 (s, 6H); 2.63 (t, 1H); 2.93–2.98 (m, 1H); 3.12 (d, 1H); 3.43 (m, 1H); 3.80 (m, 1H); 4.61 (m, 1H); 5.36 (s, 1H); 8.03 (s, 1H).

Example 17

3,8-dimethyl-12-(4-methylpiperidino)-4,14-dioxo-5,9,15-trioxatetracyclo[11.2.1.0$^{2,6}$.0$^{8,10}$]hexadec-13(16)-en-11-yl acetate Acetic anhydride (150 μmol; 15 μl) is added to a solution of the compound of Example 9 (100 μmol; 40 mg) in pyridine (0.5 ml). The solution obtained is stirred for 20 hours then the reaction mass is poured into water. The aqueous phase is extracted twice with ethyl acetate and the organic phase obtained is washed with water then with a solution of sodium chloride. The organic phase is dried over magnesium sulphate, filtered then evaporated. The residue is eluted on silica with a mixture of isopropyl acetate and dichloromethane (20/80). 16 mg of product is obtained in the form of a white powder.

NMR-$^1$H (DMSO): 0.90 (d, 3H); 1.11 (s, 3H); 1.26 (d, 3H); 1.35 (m, 1H); 1.60 (m, 2H), 1.94 (dd, 1H); 2.03 (d, 1H); 2.09 (s, 3H); 2.43 (t, 1H); 2.60 (t, 1H); 2.98 (d, 1H); 2.94–3.05 (m, 2H); 3.36–3.45 (m, 4H); 4.07 (d, 1H); 4.64 (dd, 1H); 4.70 (m, 1H); 5.38 (s, 1H); 8.12 (s, 1H).

Example 18

3,8-dimethyl-12-(4-methylpiperidino)-4,14-dioxo-11-phenylcarbonyloxy-5,9,15-trioxatetracyclo[11.2.1.0$^{2,6}$.0$^{8,10}$]hexadec-13(16)-ene Benzoyl chloride (400 μmol; 46 μl) is added to a solution of the compound of Example 9 (100 μmol; 40 mg) in pyridine (0.5 ml). The reaction mass is stirred for 2 hours then treated in the same manner as for the preparation of the compound of Example 17. 25 mg of product is obtained in the form of a white powder. Melting point: 234° C.

NMR-$^1$H (DMSO): 0.73 (d, 3H); 1.18 (s, 3H); 1.25 (m, 1H); 1.27 (d, 3H); 1.45–1.60 (m, 2H); 2.00 (dd, 1H); 2.10 (m, 1H); 2.65 (t, 1H); 2.92–3.15 (m, 3H); 3.45 (m, 2H); 3.54 (d, 1H); 4.18 (d, 1H); 4.36 (t, 1H); 4.74 (m, 1H); 4.95 (t, 1H); 5.41 (s, 1H); 7.58 (t, 2H); 7.70 (t, 1H); 8.01 (d, 2H); 8.19 (s, 1H).

Example 19 ethyl 3,8-dimethyl-12-(4-methylpiperidino)-4,14-dioxo-5,9,15-trioxatetracyclo[11.2.1.0$^{2,6}$.0$^{8,10}$]hexadec-13(16)-en-11-yl carbonate Ethyl chloroformate (300 μmol; 28 μl) is added to a solution of the compound of Example 9 (100 μmol; 40 mg) in pyridine (0.5 ml). The reaction mass is stirred for 2 hours then treated in the same manner as for the preparation of the compound of Example 17. 20 mg of product is obtained in the form of a white powder.

NMR-$^1$H (DMSO): 0.88 (d, 3H); 1.10–1.40 (m, 12H); 1.59 (m, 2H); 2.90–2.10 (m, 2H); 2.35–2.50 (m, 2H); 2.58 (t, 1H); 2.80 (d, 1H); 2.95–3.07 (m, 2H); 3.40 (d, 1H); 4.11–4.25 (m, 3H); 4.43 (dd, 1H); 4.70 (m, 1H); 5.39 (s, 1H); 8.13 (s, 1H).

Example 20

11-hydroxy-12-isobutylsulphanyl-3-isobutylsulphanylmethyl-8-methyl-5,9,15-trioxatetracyclo[11.2.1.0$^{2,6}$.0$^{8,10}$]hexadec-13(16)-ene-4,14-dione 2-methyl-1-propanethiol (500 μmol; 54 μl) is added to a solution of mikanolide (100 μmol; 30 mg) and dimethylaminopyridine (10 μmol; 1.2 mg) in acetone (1 ml). The reaction mass is stirred for two hours at ambient temperature then the solvent is evaporated off under reduced pressure. The residue is taken up in ether, the precipitate is filtered, washed with ether and dried under vacuum. 35 mg of product is obtained in the form of a white powder.

NMR-$^1$H (DMSO): 0.96 (m, 12H); 1.15 (s, 3H); 1.77 (m, 2H); 1.93 (d, 2H); 2.50 (m, 4H); 2.80–2.98 (m, 4H); 3.39 (m, 1H); 3.76 (m, 1H); 4.07 (d, 1H); 4.62 (q, 1H); 5.52 (s, 1H); 5.62 (s, 1H); 8.06 (s, 1H).

Example 21

11-hydroxy-12-isobutylsulphanyl-3,8-dimethyl-5,9,15-trioxatetracyclo[11.2.1.0$^{2,6}$.0$^{8,10}$]hexadec-13(16)-ene-4,1 4-dione 2-methyl-1-propanethiol (500 μmol; 54 μl) is added to a solution of dihydromikanolide (100 μmol; 30 mg) and dimethylaminopyridine (10 μmol; 1.2 mg) in acetone (1 ml). The reaction mass is stirred for two hours at ambient temperature then the solvent is evaporated off under reduced pressure. The residue is taken up in ether then the precipitate formed is filtered, washed with ether and dried under vacuum. 25 mg of product is obtained in the form of a white powder.

NMR-$^1$H (DMSO): 0.96 (t, 6H); 1.13 (s, 3H); 1.25 (d, 3H); 1.78 (m, 1H); 1.89 (dd, 1H); 2.00 (t, 1H); 2.48 (m, 2H); 2.62 (t, 2H); 2.82 (d, 1H); 2.98 (m, 1H); 3.78 (m, 1H); 4.07 (d, 1H); 4.57 (m, 1H); 5.40 (s, 1H); 5.61 (d, 1H); 8.06 (s, 1H)

Example 22

12-(dimethylamino)-3,8-dimethyl-4,14-dioxo-5,9,15-trioxatetracyclo[11.2.1.0$^{2,6}$.0$^{8,10}$]hexadec-13(16)-en-11-yl benzoate This compound is obtained by a procedure similar to that described for the synthesis of the compound of Example 18. The expected product is obtained in the form of a white powder.

NMR-$^1$H (DMSO):1.21 (s, 3H); 1.28 (d, 3H); 1.98 (dd, 1H); 2.08 (t, 1H); 2.48 (s, 6H); 2.66 (t, 1H); 3.01 (m, 1H); 3.51 (d, 1H); 4.04 (d, 1H); 4.71 (m, 1H); 5.06 (dd, 1H); 4.43 (s, 1H); 7.58 (m, 2H); 7.70 (t, 1H); 8.01 (d, 2H); 8.20 (s, 1H).

Example 23

12-(dimethylamino)-3,8-dimethyl-4,14-dioxo-5,9,15-trioxatetracyclo[11.2.1.0$^{2,6}$.0$^{8,10}$]hexadec-13(16)-en-11-yl acetate This compound is obtained by a procedure similar to that described for the synthesis of the compound of Example 17. The expected product is obtained in the form of a white powder.

NMR-$^1$H (DMSO):1.14 (s, 3H); 1.26 (d, 3H); 1.94 (dd, 1H); 2.05 (t, 1H); 2.08 (s, 3H); 2.45 (s, 6H); 2.62 (t, 1H); 3.97 (m, 1H); 3.32 (m, 1H); 3.90 (d, 1H); 4.68 (m, 1H); 4.78 (m, 1H); 5.39 (s, 1H); 8.12 (s, 1H).

Example 24

12-(dimethylamino)-3,8-dimethyl-4,14-dioxo-5,9,15-trioxatetracyclo[11.2.1.0$^{2,6}$.0$^{8,10}$]hexadec-13(16)-en-11-yl cyclohexanecarboxylate This compound is obtained by a procedure similar to that described for the synthesis of the compound of Example 18. The expected product is obtained in the form of a white powder.

NMR-$^1$H (DMSO): 1.14 (s, 3H); 1.26 (d, 3H); 1.08–1.48 (m, 5H); 1.58 (m, 1H); 1.68 (m, 2H); 1.84 (t, 2H); 1.93 (dd, 1H); 2.03 (t, 1H); 2.37 (m, 1H); 2.44 (s, 6H); 2.61 (t, 1H); 2.98 (m, 1H); 3.32 (t, 1H); 3.87 (d, 1H); 4.66 (m, 1H); 4.77 (dd, 1H); 5.40 (s, 1H); 8.12 (s, 1H).

Example 25

12-(dimethylamino)-3,8-dimethyl-4,14-dioxo-5,9, 15-trioxatetracyclo[11.2.1.0$^{2,6}$.0$^{8,10}$]hexadec-13(16)-en-11-yl 4-fluorobenzoate This compound is obtained by a procedure similar to that described for the synthesis of the compound of Example 18. The expected product is obtained in the form of a white powder.

NMR-$^1$H (DMSO): 1.20 (s, 3H); 1.28 (d, 3H); 1.97 (dd, 1H); 2.08 (t, 1H); 2.46 (s, 6H); 2.65 (t, 1H); 3.00 (m, 1H); 3.50 (d, 1H); 4.04 (d, 1H); 4.71 (m, 1H); 5.04 (dd, 1H); 5.43 (s, 1H); 7.41 (t, 2H); 8.06 (dd, 2H); 8.20 (s, 1H).

Example 26

11-{[tert-butyl(dimethyl)silyl]oxy}-12-(dimethylamino)-3,8-dimethyl-5,9,15-trioxatetracyclo[11.2.1.0$^{2,6}$.0$^{8,10}$]hexadec-13(16)-ene-4,14-dione hydrochloride A solution of hydrochloric acid (0.3 mmol; 0.3 ml; 1N in ether) is added to a solution of the compound of Example 16

(0.22 mmol; 100 mg) in acetone (2 ml). The precipitate is filtered, washed with a little acetone, with ether and dried under reduced pressure. 70 mg of the expected product is obtained in the form of a white powder.

NMR-$^1$H (DMSO): 0.14 (d, 6H); 0.90 (s, 9H); 1.15 (s, 3H); 1.27 (d, 3H); 1.85 (dd, 1H); 2.05 (t, 1H); 2.72 (t, 1H); 2.90–3.25 (m, 7H); 3.72 (m, 1H); 3.93 (m, 1H); 4.76 (m, 2H); 5.46 (s, 1H); 8.70 (d, 1H); 11.64 (s, 1H).

Example 27

12-(dimethylamino)-3,8-dimethyl-4,14-dioxo-5,9, 15-trioxatetracyclo[11.2.1.0$^{2,6}$.0$^{8,10}$]hexadec-13(16)-en-11-yl heptanoate This compound is obtained by a procedure similar to that described for the synthesis of the compound of Example 18. The expected product is obtained in the form of a white powder.

NMR-$^1$H (DMSO): 0.86 (t, 3H); 1.14 (s, 3H); 1.20–1.35 (m, 9H); 1.55 (m, 2H); 1.95 (dd, 1H); 2.02 (t, 1H); 2.35 (t, 2H); 2.44 (s, 6H); 2.61 (t, 1H); 2.96 (m, 1H); 3.33 (t, 1H); 3.89 (d, 1H); 4.68 (m, 1H); 4.77 (dd, 1H); 5.40 (s, 1H); 8.12 (s, 1H).

Example 28

12-(dimethylamino)-3,8-dimethyl-4,14-dioxo-5,9, 15-trioxatetracyclo[11.2.1.0$^{2,6}$.0$^{8,10}$]hexadec-13(16)-en-11-yl 4-(trifluoromethyl)benzoate This compound is obtained by a procedure similar to that described for the synthesis of the compound of Example 18. The expected product is obtained in the form of a white powder.

NMR-$^1$H (DMSO):1.21 (s, 3H); 1.28 (d, 3H); 2.01 (dd, 1H); 2.06 (t, 1H); 2.48 (s, 6H); 2.66 (t, 1H); 3.00 (m, 1H); 3.55 (d, 1H); 4.09 (d, 1H); 4.73 (m, 1H); 5.04 (dd, 1H); 5.44 (s, 1H); 7.96 (d, 2H); 8.19 (d, 2H); 8.21 (s, 1H).

Example 29

12-(dimethylamino)-3,8-dimethyl-4,14-dioxo-5,9, 15-trioxatetracyclo[11.2.1.0$^{2,6}$.0$^{8,10}$]hexadec-13(16)-en-11-yl 2-thiophenecarboxylate This compound is obtained by a procedure similar to that described for the synthesis of the compound of Example 18. The expected product is obtained in the form of a white powder.

NMR-$^1$H (DMSO): 1.20 (s, 3H); 1.27 (d, 3H); 1.99 (m, 1H); 2.07 (t, 1H); 2.49 (s, 6H); 2.65 (t, 1H); 3.00 (m, 1H); 3.47 (d, 1H); 4.00 (d, 1H); 4.70 (m, 1H); 5.01 (dd, 1H); 5.43 (s, 1H); 7.26 (t, 1H); 7.87 (d, 1H); 8.01 (dd, 1H); 8.18 (s, 1H).

Example 30

12-(dimethylamino)-3,8-dimethyl-4,14-dioxo-5,9, 15-trioxatetracyclo[11.2.1.0$^{2,6}$.0$^{8,10}$]hexadec-13(16)-en-11-yl 3,3-dimethylbutanoate This compound is obtained by a procedure similar to that described for the synthesis of the compound of Example 18. The expected product is obtained in the form of a white powder.

NMR-$^1$H (DMSO): 1.00 (s, 9H); 1.15 (s, 3H); 1.26 (d, 3H); 1.94 (dd, 1H); 2.03 (t, 1H); 2.24 (dd, 2H); 2.45 (s, 6H); 2.62 (t, 1H); 2.98 (m, 1H); 3.32 (d, 1H); 3.86 (d, 1H); 4.65 (m, 1H); 4.81 (dd, 1H); 5.40 (s, 1H); 8.12 (s, 1H).

Example 31

12-(dimethylamino)-3,8-dimethyl-4,14-dioxo-5,9, 15-trioxatetracyclo[11.2.1.0$^{2,6}$.0$^{8,10}$]hexadec-13(16)-en-11-yl 1-benzothiophene-2-carboxylate This compound is obtained by a procedure similar to that described for the synthesis of the compound of Example 18. The expected product is obtained in the form of a white powder.

NMR-$^1$H (DMSO): 1.22 (s, 3H); 1.28 (d, 3H); 2.01 (dd, 1H); 2.08 (m, 1H); 2.50 (s, 6H); 2.66 (t, 1H); 3.00 (m, 1H); 3.52 (d, 1H); 4.05 (d, 1H); 4.71 (m, 1H); 5.06 (dd, 1H); 5.44 (s, 1H); 7.50 (t, 1H); 7.56 (t, 1H); 8.09 (t, 2H); 8.21 (s, 1H); 8.27 (s, 1H).

Example 32

12-(dimethylamino)-3,8-dimethyl-4,14-dioxo-5,9, 15-trioxatetracyclo[11.2.1.0$^{2,6}$.0$^{8,10}$]hexadec-13(16)-en-11-yl 2-furoate This compound is obtained by a procedure similar to that described for the synthesis of the compound of Example 18. The expected product is obtained in the form of a white powder.

NMR-$^1$H (DMSO): 1.19 (s, 3H); 1.27 (d, 3H); 1.97 (dd, 1H); 2.07 (t, 1H); 2.47 (s, 6H); 2.64 (t, 1H); 3.00 (m, 1H); 3.46 (d, 1H); 4.00 (d, 1H); 4.70 (m, 1H); 4.98 (dd, 1H); 5.43 (s, 1H); 6.72 (d, 1H); 7.36 (d, 1H); 8.03 (s, 1H); 8.18 (s, 1H).

Example 33

12-(dimethylamino)-3,8-dimethyl-4,14-dioxo-5,9, 15-trioxatetracyclo[11.2.1.0$^{2,6}$.0$^{8,10}$]hexadec-13(16)-en-11-yl 5-nitro-2-furoate This compound is obtained by a procedure similar to that described for the synthesis of the compound of Example 18. The expected product is obtained in the form of a white powder.

NMR-$^1$H (DMSO): 1.19 (s, 3H); 1.28 (d, 3H); 1.98 (dd, 1H); 2.08 (t, 1H); 2.45 (s, 6H); 2.64 (t, 1H); 3.00 (m, 1H); 3.53 (d, 1H); 4.08 (d, 1H); 4.72 (m, 1H); 4.97 (dd, 1H); 5.44 (s, 1H); 7.65 (d, 1H); 7.80 (d, 1H); 8.21 (s, 1H).

Example 34

12-(dimethylamino)-3,8-dimethyl-4,14-dioxo-5,9, 15-trioxatetracyclo[11.2.1.0$^{2,6}$.0$^{8,10}$]hexadec-13(16)-en-11-yl 2-thiophenecarboxylate hydrochloride A solution of hydrochloric acid (0.8 mmol; 0.8 ml; 1N in ether) is added to a solution of the compound of Example 29 (0.44 mmol; 196 mg) in acetone (4 ml). The precipitate is filtered, washed with a little acetone, with ether and dried under reduced pressure. 180 mg of the expected product is obtained in the form of a white powder.

NMR-$^1$H (DMSO): 1.23 (s, 3H); 1.29 (d, 3H); 1.90 (dd, 1H); 2.13 (t, 1H); 2.76 (t, 1H); 2.85–3.25 (m, 7H); 3.95 (m, 1H); 4.78 (m, 1H); 5.02 (m, 1H); 5.38 (m, 1H); 5.51 (s, 1H); 7.29 (t, 1H); 7.97 (s, 1H); 8.08 (d, 1H); 8.86 (s, 1H); 12.12 (s, 1H).

Example 35

12-(dimethylamino)-3,8-dimethyl-4,14-dioxo-5,9, 15-trioxatetracyclo[11.2.1.0$^{2,6}$.0$^{8,10}$]hexadec-13(16)-en-11-yl 2-thienylacetate This compound is obtained by a procedure similar to that described for the synthesis of the compound of Example 18. The expected product is obtained in the form of a white powder.

NMR-¹H (DMSO): 1.14 (s, 3H); 1.26 (d, 3H); 1.94 (dd, 1H); 2.04 (m, 1H); 2.38 (s, 6H); 2.61 (t, 1H); 2.97 (m, 1H); 3.37 (d, 1H); 3.88 (d, 1H); 4.00 (d, 2H); 4.68 (m, 1H); 4.78 (dd, 1H); 5.39 (s, 1H); 6.98 (m, 2H); 7.43 (d, 1H); 8.12 (s, 1H).

Example 36

12-(dimethylamino)-3,8-dimethyl-4,14-dioxo-5,9,15-trioxatetracyclo[11.2.1.0$^{2,6}$.0$^{8,10}$]hexadec-13(16)-en-11-yl phenoxyacetate This compound is obtained by a procedure similar to that described for the synthesis of the compound of Example 18. The expected product is obtained in the form of a white powder.

NMR-¹H (DMSO): 1.23 (s, 3H); 1.35 (d, 3H); 2.04 (dd, 1H); 2.13 (t, 1H); 2.58 (s, 6H); 2.67 (t, 1H); 3.06 (m, 1H); 3.48 (d, 1H); 4.08 (d, 1H); 4.77 (m, 1H); 4.86 (m, 1H); 4.96 (dd, 2H); 5.50 (s, 1H); 7.05 (m, 3H); 7.38 (m, 2H); 8.23 (s, 1H).

Example 37

8-(dimethylamino)-3,10a-dimethyl-2,6-dioxodecahydro-4,7-methenofuro[3,2-c]oxireno[f]oxacycloundecin-9-yl 4-tert-butylphenylcarbamate 4-terbutylphenylisocyanate (250 μmol; 44 mg) is added to a solution of the compound of Example 5 (200 μmol; 67 mg) in 1,2-dichloroethane (10 ml). The solution obtained is stirred for 20 hours at 60° C. before evaporating the solvent under reduced pressure. The residue is eluted on silica using a mixture of acetone and dichloromethane (20/80). The residue is taken up in ether, filtered and dried under vacuum. 36 mg of product is obtained in the form of a white powder.

NMR-¹H (DMSO): 1.18 (s, 3H); 1.25 (s, 9H); 1.27 (d, 3H); 1.95 (dd, 1H); 2.08 (t, 1H); 2.48 (s, 6H); 2.64 (t, 1H); 2.98 (m, 1H); 3.37 (m, 1H); 3.91 (d, 1H); 4.69 (m, 1H); 4.80 (dd, 1H); 5.40 (s, 1H); 7.29 (d, 2H); 7.38 (d, 2H); 8.12 (s, 1H); 9.67 (s, 1H).

Example 38

8-(dimethylamino)-3,10a -dimethyl-2,6-dioxodecahydro-4,7-methenofuro[3,2-c]oxireno[f]oxacycloundecin-9-yl thien-2-ylcarbamate This compound is obtained by a procedure similar to that described for the synthesis of the compound of Example 18. The expected product is obtained in the form of a white powder.

NMR-¹H (DMSO): 1.18 (s, 3H); 1.26 (d, 3H); 1.95 (m, 1H); 2.06 (m, 1H); 2.48 (s, 6H); 2.64 (t, 1H); 2.97 (m, 1H); 3.36 (m, 1H); 3.90 (m, 1H); 4.68 (m, 1H); 4.79 (m, 1H); 5.40 (s, 1H); 6.61 (s, 1H); 6.82 (s, 1H); 6.94 (s, 1H); 8.13 (s, 1H); 10.78 (s, 1H).

Example 39

8-(dimethylamino)-3,10a -dimethyl-2,6-dioxodecahydro-4,7-methenofuro[3,2-c]oxireno[f]oxacycloundecin-9-yl 2-methoxyphenylcarbamate This compound is obtained by a procedure similar to that described for the synthesis of the compound of Example 18. The expected product is obtained in the form of a white powder.

NMR-¹H (DMSO): 1.17 (s, 3H); 1.27 (d, 3H); 1.94 (dd, 1H); 2.05 (t, 1H); 2.48 (s, 6H); 2.63 (t, 1H); 2.98 (m, 1H); 3.37 (m, 1H); 3.80 (s, 3H); 3.87 (d, 1H); 4.68 (m, 1H); 4.80 (dd, 1H); 5.40 (s, 1H); 6.90 (t, 1H); 7.02 (d, 1H); 7.09 (t, 1H); 7.59 (d, 1H); 8.12 (s, 1H); 8.59 (s, 1H).

Example 40

8-(dimethylamino)-3,10a -dimethyl-2,6-dioxodecahydro-4,7-metheno-furo[3,2-c]oxireno[f]oxacycloundecin-9-yl 2(methylthio)phenylcarbamate This compound is obtained by a procedure similar to that described for the synthesis of the compound of Example 18. The expected product is obtained in the form of a white powder.

NMR-¹H (DMSO): 1.17 (s, 3H); 1.27 (d, 3H); 1.95 (dd, 1H); 2.08 (t, 1H); 2.40 (s, 3H); 2.48 (s, 6H); 2.63 (t, 1H); 2.98 (m, 1H); 3.34 (m, 1H); 3.84 (d, 1H); 4.67 (m, 1H); 4.80 (dd, 1H); 5.39 (s, 1H); 7.15–7.25 (m, 3H); 7.32 (t, 1H); 8.10 (s, 1H); 8.90 (s, 1H).

Example 41

8-(dimethylamino)-3,10a-dimethyl-2,6-dioxodecahydro-4,7-methenofuro[3,2-c]oxireno[f]oxacycloundecin-9-yl 2-ethoxyphenylcarbamate This compound is obtained by a procedure similar to that described for the synthesis of the compound of Example 18. The expected product is obtained in the form of a white powder.

NMR-¹H (DMSO): 1.17 (s, 3H); 1.27 (d, 3H); 1.35 (t, 3H); 1.95 (dd, 1H); 2.05 (t, 1H); 2.48 (s, 6H); 2.63 (t, 1H); 2.98 (m, 1H); 3.34 (m, 1H); 3.90 (d, 1H); 4.07 (q, 2H); 4.67 (m, 1H); 4.79 (dd, 1H); 5.40 (s, 1H); 6.90 (t, 1H); 7.01 (d, 1H); 7.07 (t, 1H); 7.58 (d, 1H); 8.12 (s, 1H); 8.46 (s, 1H).

Example 42

8-(dimethylamino)-3,10a-dimethyl-2,6-dioxodecahydro-4,7-methenofuro[3,2-c]oxireno[f]oxacycloundecin-9-yl thien-3-ylcarbamate This compound is obtained by a procedure similar to that described for the synthesis of the compound of Example 18. The expected product is obtained in the form of a white powder.

NMR-¹H (DMSO): 1.18 (s, 3H); 1.27 (d, 3H); 1.95 (dd, 1H); 2.05 (m, 1H); 2.48 (s, 6H); 2.64 (t, 1H); 2.98 (m, 1H); 3.36 (m, 1H); 3.90 (d, 1H); 4.68 (m, 1H); 4.80 (dd, 1H); 5.40 (s, 1H); 7.04 (d, 1H); 7.22 (s, 1H); 7.43 (t, 1H); 8.12 (s, 1H); 10.08 (s, 1H).

Example 43

8-(dimethylamino)-3,10a-dimethyl-2,6-dioxodecahydro-4,7-methenofuro[3,2-c]oxireno[f]oxacycloundecin-9-yl 1-benzothien-3-ylcarbamate This compound is obtained by a procedure similar to that described for the synthesis of the compound of Example 18. The expected product is obtained in the form of a white powder.

NMR-¹H (DMSO): 1.20 (s, 3H); 1.28 (d, 3H); 1.98 (dd, 1H); 2.07 (m, 1H); 2.48 (s, 6H); 2.65 (t, 1H); 2.98 (m, 1H); 3.40 (m, 1H); 3.97 (d, 1H); 4.70 (m, 1H); 4.82 (dd, 1H); 5.40 (s, 1H); 7.40 (m, 2H); 7.65 (s, 1H); 7.95 (d, 1H); 8.14 (m, 2H); 10.00 (s, 1H).

Example 44

8-(dimethylamino)-3,10a -dimethyl-2,6-dioxodecahydro-4,7-metheno-furo[3,2-c]oxireno[f]oxacycloundecin-9-yl N-(ter-butoxycarbonyl)glycinate 1-(3-dimethylaminopropyl)-3-ethylcarbodiimide hydrochloride (200 μmol; 38 mg), N-terbutyloxycarbonylglycine (200 μmol; 35 mg), triethylamine (200 μmol; 28 μl) and dimethylaminopyridine (10 μmol; 3mg) are added to a solution of the compound of Example 5 (200 μmol; 60 mg) in dichloromethane (5 ml). The solution is stirred for three hours at ambient temperature, poured into a solution of NaHCO$_3$ then extracted with ethyl acetate. The organic phase is washed with water then with a saturated solution of sodium chloride before being dried over MgSO$_4$ and filtered. The solvent is eliminated by distillation under reduced pressure. The residue is eluted on silica using a mixture of acetone and dichloromethane (40/60). The residue is taken up in ether, filtered and dried under vacuum. 25 mg of product is obtained in the form of a white powder.

NMR-$^1$H (DMSO): 1.15 (s, 3H); 1.26 (d, 3H); 1.39 (s, 9H); 1.92 (dd, 1H); 2.05 (t, 1H); 2.43 (s, 6H); 2.62 (t, 1H); 2.98 (m, 1H); 3.35 (t, 1H); 3.75 (t, 2H); 3.84 (d, 1H); 4.67 (m, 1H); 4.81 (dd, 1H); 5.40 (s, 1H); 7.25 (t, 1H); 8.13 (s, 1H).

Example 45

8-(dimethylamino)-3,10a-dimethyl-2,6-dioxodecahydro-4,7-methenofuro[3,2-c]oxireno[f] oxacycloundecin-9-yl thien-3-ylacetate This compound is obtained by a procedure similar to that described for the synthesis of the compound of Example 44. The expected product is obtained in the form of a white powder.

NMR-$^1$H (DMSO): 1.14 (s, 3H); 1.26 (d, 3H); 1.94 (dd, 1H); 2.05 (m, 1H); 2.37 (s, 6H); 2.61 (t, 1H); 2.97 (m, 1H); 3.33 (t, 1H); 3.77 (s, 2H); 3.88 (d, 1H); 4.67 (m, 1H); 4.78 (dd, 1H); 5.39 (s, 1H); 7.04 (d, 1H); 7.36 (s, 1H); 7.50 (t, 1H); 8.11 (s, 1H).

Example 46

8-(dimethylamino)-3,10a -dimethyl-2,6-dioxodecahydro-4,7-methenofuro[3,2-c]oxireno[f] oxacycloundecin-9-yl 1-benzothien-3-ylacetate This compound is obtained by a procedure similar to that described for the synthesis of the compound of Example 44. The expected product is obtained in the form of a white powder.

NMR-$^1$H (DMSO): 1.13 (s, 3H); 1.25 (d, 3H); 1.94 (dd, 1H); 2.04 (t, 1H); 2.26 (s, 6H); 2.60 (t, 1H); 2.96 (m, 1H); 3.32 (m, 1H); 3.88 (d, 1H); 4.04 (s, 2H); 4.67 (m, 1H); 4.74 (dd, 1H); 5.38 (s, 1H); 7.40 (m, 2H); 7.64 (s, 1H); 7.79 (d, 1H); 7.99 (d, 1H); 8.09 (s, 1H).

Example 47

8-(dimethylamino)-3,10a -dimethyl-2,6-dioxodecahydro-4,7-methenofuro[3,2-c]oxireno[f] oxacycloundecin-9-yl thiophene-3-carboxylate This compound is obtained by a procedure similar to that described for the synthesis of the compound of Example 44. The expected product is obtained in the form of a white powder.

NMR-$^1$H (DMSO): 1.19 (s, 3H); 1.27 (d, 3H); 1.97 (dd, 1H); 2.07 (t, 1H); 2.48 (s, 6H); 2.65 (t, 1H); 2.99 (m, 1H); 3.46 (d, 1H); 3.98 (s, 1H); 4.70 (m, 1H); 5.02 (m, 1H); 5.43 (s, 1H); 7.49 (s, 1H); 7.69 (s, 1H); 8.18 (s, 1H); 8.40 (s, 1H).

Example 48

8-(dimethylamino)-3,10a -dimethyl-2,6-dioxodecahydro-4,7-methenofuro[3,2-c]oxireno[f] oxacycloundecin-9-yl 5-phenylthien-2-ylcarbamate This compound is obtained by a procedure similar to that described for the synthesis of the compound of Example 37. The expected product is obtained in the form of a white powder.

NMR-$^1$H (DMSO): 1.20 (s, 3H); 1.27 (d, 3H); 1.97 (dd, 1H); 2.03 (t, 1H); 2.38 (s, 6H); 2.67 (m, 1H); 2.98 (m, 1H); 3.37 (d, 1H); 3.94 (m, 1H); 4.69 (m, 1H); 4.81 (m, 1H); 5.41 (s, 1H); 6.60 (s, 1H); 7.22 (m, 2H); 7.36 (t, 2H); 7.55 (d, 2H); 8.14 (s, 1H); 10.93 (s, 1H).

Example 49

8-(dimethylamino)-3,10a -dimethyl-2,6-dioxodecahydro-4,7-methenofuro[3,2-c]oxireno[f] oxacycloundecin-9-yl 1-adamantylcarbamate This compound is obtained by a procedure similar to that described for the synthesis of the compound of Example 37. The expected product is obtained in the form of a white powder.

NMR-$^1$H (DMSO): 1.14 (s, 3H); 1.26 (d, 3H); 1.60 (s, 6H); 1.80–1.94 (m, 6H); 1.94–2.09 (m, 4H); 2.47 (s, 6H); 2.62 (t, 1H); 2.96 (m, 1H); 3.21 (d, 1H); 3.38 (s, 1H); 3.76 (s, 1H); 4.64 (m, 2H); 5.37 (s, 1H); 6.96 (s, 1H); 8.05 (s, 1H).

Example 50

8-(dimethylamino)-3,10a-dimethyl-2,6-dioxodecahydro-4,7-methenofuro[3,2-c]oxireno[f] oxacycloundecin-9-yl 2-naphthylcarbamate This compound is obtained by a procedure similar to that described for the synthesis of the compound of Example 37. The expected product is obtained in the form of a white powder.

NMR-$^1$H (DMSO): 1.20 (s, 3H); 1.28 (d, 3H); 1.96 (dd, 1H); 2.07 (t, 1H); 2.48 (s, 6H); 2.66 (t, 1H); 3.01 (m, 1H); 3.37 (m, 1H); 3.95 (d, 1H); 4.70 (m, 1H); 4.87 (dd, 1H); 5.42 (s, 1H); 7.38 (t, 1H); 7.46 (t, 1H); 7.55 (d, 1H); 7.82 (m, 3H); 8.10 (s, 1H); 8.14 (s, 1H); 10.01 (s, 1H).

Example 51

8-(dimethylamino)-3,10a -dimethyl-2,6-dioxodecahydro-4,7-metheno-furo[3,2-c]oxireno[f] oxacycloundecin-9-yl 2-tert-butyl-6-methylphenylcarbamate This compound is obtained by a procedure similar to that described for the synthesis of the compound of Example 37. The expected product is obtained in the form of a white powder.

NMR-$^1$H (DMSO): 1.14 (s, 3H); 1.20–1.42 (m, 12H); 1.92 (dd, 1H); 2.05 (m, 1H); 2.25 (s, 3H); 2.52 (s, 6H); 2.62 (m, 1H); 2.95 (m, 1H); 3.36 (m, 1H); 3.88 (m, 1H); 4.80–4.95 (m, 2H); 5.40 (s, 1H); 7.13 (m, 2H); 7.22 (s, 1H); 8.13 (s, 1H); 8.69 (s, 1H).

Example 52

8-(dimethylamino)-3,10a-dimethyl-2,6-dioxodecahydro-4,7-metheno-furo[3,2-c]oxireno[f] oxa-cycloundecin-9-yl 2,5-dimethoxyphenylcarbamate This compound is obtained by a procedure similar to that described for the synthesis of the compound of Example 37. The expected product is obtained in the form of a white powder.

NMR-$^1$H (DMSO): 1.17 (s, 3H); 1.27 (d, 3H); 1.94 (dd, 1H); 2.06 (m, 1H); 2.48 (s, 6H); 2.64 (t, 1H); 2.98 (m, 1H); 3.33 (m, 1H); 3.69 (s, 3H); 3.76 (s, 3H); 3.89 (d, 1H); 4.68 (m, 1H); 4.80 (dd, 1H); 5.40 (s, 1H); 6.63 (d, 1H); 6.94 (d, 1H); 7.32 (s, 1H); 8.12 (s, 1H); 8.58 (s, 1H).

Pharmacological Study of the Compounds of the Invention

The usefulness of the compounds of the invention can be demonstrated in particular by the effect of a treatment with these compounds on:

- the incorporation of cytosine labelled with $^{32}P$ in a DNA fragment in the presence of DNA polymerase of *E. Coli* (acellular system);
- the incorporation of tritiated thymidine in the DNA of HT29 tumor cells in division over a period of 3 hours (cell system); and
- the proliferation of two human cell lines Mia-Paca2 and DU145.

1) Procedures

Cell Lines

DU-145 (human prostate cancer cells), HT29 (cancer of the colon) and Mia-PaCa2 (human pancreatic cancer cells) were acquired from the American Tissue Culture Collection (Rockville, Md., USA).

Incorporation of Deoxycytidine 5'-[alpha$^{32}$P]-triphosphate into a DNA in the Presence of DNA Polymerase in an Acellular System Labelling of the DNA is carried out on a DNA fragment which incorporates nucleotides by way of the activity of the DNA polymerase enzyme. From these nucleotides, the dCTP is labelled with radioactive phosphorus ($^{32}P$).

Plasmidal DNA (pc DNA 3, invitrogen, Netherlands) is diluted to a concentration of 2 ng in 45 µl of TE solution (10 mM Tris-HCl, pH 8, 1 mM EDTA) and denatured by heating to 100° C. for 10 minutes before being replaced directly in ice. The denatured DNA is placed in the tube which contains the buffer solution of dATP, dGTP, dTTP, the Klenow DNA polymerase enzyme and the random primers (Rediprime II random prime labelling system, RPN 1633, RPN 1634, Amersham pharmacia biotech). 2 µl of Redivue deoxycytidine 5'-[alpha$^{32}$P]-triphosphate (250 µCi specific activity Amersham, Orsay, France) is added to start the reaction. The reaction is carried out in the presence or absence of the compound to be tested for 10 minutes at 37°. The reaction is stopped by adding 5 µl of EDTA (0.2M). The labelled DNA is recovered in 200 µl of isopropanol after centrifugation for 10 minutes at 12,000 rpm then washed with 70% ethanol. After drying completely, the DNA is solubilized in 50 µl of TE. 10 µL is counted in 5 ml of scintillator (Instage1 plus and scintillation counter Packard, Rungis, France). The results are expressed as a percentage of the inhibition of incorporation of the labelled nucleotide in the sample with respect to the control: 100–[(DPM of the sample treated/control DPM)×100].

Incorporation of Thymidine Labelled with Tritium into DNA Cells in Exponential Growth Phase HT29 cells are seeded in 96-well plates (culturPlate-96, Packard, Rungis, France) (4000 cells per well) with the medium (DME, Gibco BRL, Cergy-Pontoise, France) complemented with 10% of foetal calf serum, Gibco BRL, Cergy-Pontoise, France). On day 3, the medium is removed and replaced with medium containing the tritiated thymidine (5'-thymidine TRK.328, 1 mCi, 0.6 µCi/well, Amersham, Orsay, France) with or without the compound. The treatments are carried out for 3 hours. The medium is then removed and the cells are washed twice with 20 µl of PBS (Gibco BRL, Cergy-Pontoise, France). The lysis solution (SDS 1.25%, EDTA 5 mM) is added for 10 minutes at ambient temperature, then 75 µl of scintillating liquid (microscint 40, Packard, Rungis, France) is added. The plates are read using Topcount (Packard, Rungis, France). These tests are carried out in duplicate and the results are expressed with respect to the incorporation of the labelled nucleotide in the sample treated with the compound over the incorporation of the labelled nucleotide in the control sample (sample DPM/control DPM).

Measurement of Cell Proliferation

The cells placed in 80 µl of Dulbecco's modified Eagle medium (Gibco-BRL, Cergy-Pontoise, France) completed with 10% of foetal calf serum inactivated by heating (Gibco-BRL, Cergy-Pontoise, France), 50000 units/l of penicillin and 50 mg/l streptomycin (Gibco-BRL, Cergy-Pontoise, France), and 2 mM of glutamine (Gibco-BRL, Cergy-Pontoise, France) were seeded on a 96-well plate on day 0. The cells were treated on day 1 for 96 hours with increasing concentrations of each of the compounds to be tested. At the end of the of this period, quantification of the cell proliferation is evaluated by a calorimetric test based on the cleavage of the tetrazolium salt WST1 by mitochondrial dehydrogenases in viable cells leading to the formation of formazan (Boehringer Mannheim, Meylan, France). These tests are carried out in duplicate with 8 determinations per concentration tested. The products are solubilised in dimethylsulphoxide (DMSO) at $10^{-2}$ M and finally used in culture with 0.5% DMSO.

2) Results

At a concentration of 100 µg/ml, the compound of Example 16, like dihydromikanolide, inhibits the activity of DNA polymerase in an acellular system (Table I).

TABLE I

| | % inhibition of incorporation |
|---|---|
| Dihydromikanolide | 77 ± 11 |
| Example 16 | 70 ± 8 |

Moreover, the compound of Example 16, like dihydromikanolide, inhibits the incorporation of tritiated thymidine in the DNA of human HT29 cells (Table II).

TABLE II

| | (sample dpm/control dpm) | | |
|---|---|---|---|
| Concentration µg/ml | 100 | 50 | 25 |
| Dihydromikanolide | 0.14 | 0.22 | 0.98 |
| Example 16 | 0.52 | 0.58 | 0.71 |

Finally, the compounds of Examples 1 to 3, 9, 16, 18, 22, 24 to 32 and 39 to 43 inhibit the proliferation of DU-145 cell lines with an $IC_{50}$ inhibitory concentration lower than or equal to 30 µM, whereas the compounds of Examples 1 to 10, 12, 16 to 20, 22, 24 to 37 and 39 to 44 inhibit the proliferation of the Mia-Paca2 cell lines with an $IC_{50}$ inhibitory concentration lower than or equal to 30 µM.

What is claimed is:

1. A compound of the formula:

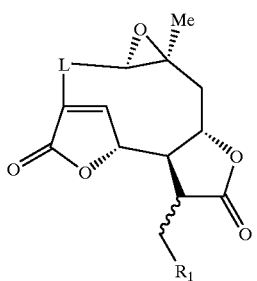

(I)

corresponding to sub-formulae:

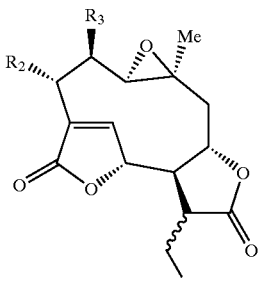

(I)$_1$

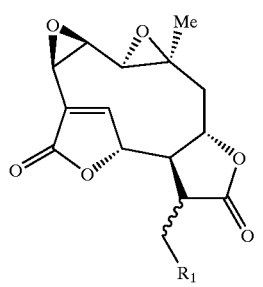

(I)$_2$ wherein $R_1$ is selected from the group consisting of hydrogen, —SR$_4$ and —NR$_4$R$_5$;

$R_2$ is —SR$_6$ or —NR$_6$R$_7$;

$R_3$ is selected from the group consisting of OH, —O(CO)R$_{14}$, —OSiR$_{15}$R$_{16}$R$_{17}$, —O(CO)OR$_{18}$ and —O(CO)NHR$_{18}$;

$R_4$ and $R_6$ are individually selected from the group consisting of, alkyl, cycloalkyl, cycloalkylalkyl, hydroxyalkyl, aryl and aralkyl optionally substituted on the aryl by at least one member of the group consisting of alkyl, hydroxy and alkoxy, $R_5$ and $R_7$ are individually selected from the group consisting of hydrogen, alkyl, cycloalkyl, cycloalkylalkyl, hydroxyalkyl, aryl and aralkyl optionally substituted on the aryl by at least one member of the group consisting of alkyl, hydroxy and alkoxy or $R_4$ and $R_5$ form together with the nitrogen atom which carries them a heterocycle with 5 to 7 ring members the additional member being selected from the group consisting of —CR$_8$R$_9$—, —NR$_{10}$—, —O— and —S—, it being understood that there can only be one member chosen from —O— or —S— in said heterocycle, or $R_6$ and $R_7$ form together with the nitrogen atom which carries them a heterocycle with 5 to 7 ring members, the additional member being selected from the group consisting of —CR$_{11}$R$_{12}$—, —NR$_{13}$—, —O— and —S— it being understood however that there can only be one member chosen from —O— or —S— in said heterocycle, $R_8$, $R_{10}$, $R_{11}$ and $R_{13}$ are individually hydrogen, alkyl, alkoxycarbonyl and aralkyl, $R_9$ and $R_{12}$ are individually hydrogen or alkyl or each of $R_9$ and $R_{12}$ being able to form respectively together with $R_8$ and $R_{11}$—O—(CH$_2$)$_2$—O— attached on either side to the carbon atom which carries it, such a radical only being present once at most per NR$_4$R$_5$ or NR$_6$R$_7$ $R_{14}$ is selected from the group consisting of alkyl, cycloalkyl, adamantyl, aryl, heteroaryl, aralkyl and heteroaralkyl optionally substituted on the aryl or heteroaryl by at least one member of the group consisting of halogen, alkyl, haloalkyl, nitro, hydroxy, alkoxy, alkylthio and phenyl;

or $R_{14}$ is such that $R_{14}$—COOH is a natural amino acid or the optical enantiomer of such an amino acid;

$R_{15}$, $R_{16}$ and $R_{17}$ are individually alkyl, or phenyl;

$R_{18}$ is selected from the group consisting of alkyl, cycloalkyl, adamantyl, aryl, heteroaryl, aralkyl and heteroaralkyl optionally substituted on the aryl or heteroaryl by at least one member of the group consisting of halogen, alkyl, haloalkyl, nitro, hydroxy, alkoxy, alkylthio and phenyl;

it being understood however that when the compounds correspond to sub-formula (I)$_2$, then $R_1$ is not hydrogen;

or a pharmaceutically acceptable salt thereof.

2. A compound of claim 1, wherein it has sub-formula (I)$_1$ or is a pharmaceutically acceptable salt thereof.

3. A compound of claim 2, wherein:

$R_1$ is hydrogen or —NR$_4$R$_5$;

$R_2$ is —NR$_6$R$_7$;

$R_3$ is selected from the group consisting of —OH, —O(CO)R$_{14}$, —OSiR$_{15}$R$_{16}$R$_{17}$ and —O(CO)NHR$_{18}$.

4. A compound of claim 1, wherein it has sub-formula (I)$_2$.

5. A compound of claim 1, selected from the group consisting of:

12-diisopropylaminomethyl-7-methyl-3,6,10,15-tetraoxapentacyclo [12.2.1.0$^{2,4}$.0$^{5,7}$.0$^{9,13}$]heptadec-1(17)-ene-11,16-dione;

12-dimethylamino-3-dimethylaminomethyl-11-hydroxy-8-methyl-5,9,15-trioxatetracyclo[11.2.1.0$^{2,6}$.0$^{8,10}$]hexadec-13(16)-ene-4,14-dione;

12-benzyl(methyl)amino-3-benzyl(methyl)aminomethyl-11-hydroxy-8-methyl-5,9,15-trioxatetracyclo [11.2.1.0$^{2,6}$.0$^{8,10}$]hexadec-13(16)-ene-4,14-dione;

11-hydroxy-8-methyl-12-morpholino-3-morpholinomethyl-5,9,15-trioxatetracyclo [11.2.1.0$^{2,6}$.0$^{8,10}$]hexadec-13(16)-ene-4,14-dione;

12-dimethylamino-11-hydroxy-3,8-dimethyl-5,9,15-trioxatetracyclo[11.2.1.0$^{2,6}$.0$^{8,10}$]hexadec-13(16)-ene-4,14-dione;

11-hydroxy-3,8-dimethyl-12-(4-methylpiperidino)-5,9,15-trioxatetracyclo[11.2.1.0$^{2,6}$.0$^{8,10}$]hexadec-13(16)-ene-4,14-dione;

11-hydroxy-3,8-dimethyl-12-pyrrolidino-5,9,15-trioxatetracyclo[11.2.1.0$^{2,6}$.0$^{8,10}$]hexadec-13(16)-ene-4,14-dione;

ethyl 1-[11-hydroxy-3,8-dimethyl-4,14-dioxo-5,9,15-trioxatetracyclo[11.2.1.0$^{2,6}$.0$^{8,10}$]hexadec-13(16)-en-12-yl]-4-piperidinecarboxylate;

12-(4-benzylpiperidino)-11-hydroxy-3,8-dimethyl-5,9,15-trioxatetracyclo[11.2.1.0$^{2,6}$.0$^{8,10}$]hexadec-13(16)-ene-4,14-dione;

11-hydroxy-3,8-dimethyl-12-piperidino-5,9,15-trioxatetracyclo[11.2.1.0$^{2,6}$.0$^{8,10}$]hexadec-13(16)-ene-4,14-dione;

12-(1,4-dioxa-8-azaspiro[4.5]dec-8-yl)-11-hydroxy-3,8-dimethyl-5,9,15-trioxatetracyclo[11.2.1.0$^{2,6}$.0$^{8,10}$]hexadec-13(16)-ene-4,14-dione;

11-hydroxy-3,8-dimethyl-12-morpholino-5,9,15-trioxatetracyclo[11.2.1.0$^{2,6}$.0$^{8,10}$]hexadec-13(16)-ene-4,14-dione;

11-(tert-butyldimethylsiloxy)-12-dimethylamino-3,8-dimethyl-5,9,15-trioxatetracyclo[11.2.1.0$^{2,6}$.0$^{8,10}$]hexadec-13(16)-ene-4,14-dione;

3,8-dimethyl-12-(4-methylpiperidino)-4,14-dioxo-5,9,15-trioxatetracyclo[11.2.1.0$^{2,6}$.0$^{8,10}$]hexadec-13(16)-en-11-yl acetate;

3,8-dimethyl-12-(4-methylpiperidino)-4,14-dioxo-11-phenylcarbonyloxy-5,9,15-trioxatetracyclo[11.2.1.0$^{2,6}$.0$^{8,10}$]hexadec-13(16)-ene;

ethyl 3,8-dimethyl-12-(4-methylpiperidino)-4,14-dioxo-5,9,15-trioxatetracyclo[11.2.1.0$^{2,6}$.0$^{8,10}$]hexadec-13(16)-en-11-yl carbonate;

11-hydroxy-12-isobutylsulphanyl-3-isobutylsulphanylmethyl-8-methyl-5,9,15-trioxatetracyclo[11.2.1.0$^{2,6}$.0$^{8,10}$]hexadec-13(16)-ene-4,14-dione;

11-hydroxy-12-isobutylsulphanyl-3,8-dimethyl-5,9,15-trioxatetracyclo[11.2.1.0$^{2,6}$.0$^{8,10}$]hexadec-13(16)-ene-4,14-dione;

12-(dimethylamino)-3,8-dimethyl-4,14-dioxo-5,9,15-trioxatetracyclo[11.2.1.02.6.08.10]hexadec-13(16)-en-11-yl benzoate;

12-(dimethylamino)-3,8-dimethyl-4,14-dioxo-5,9,15-trioxatetracyclo[11.2.1.02.6.08.10]hexadec-13(16)-en-11-yl acetate;

12-(dimethylamino)-3,8-dimethyl-4,14-dioxo-5,9,15-trioxatetracyclo[11.2.1.0$^{2,6}$.0$^{8,10}$]hexadec-13(16)-en-11-yl cyclohexanecarboxylate;

12-(dimethylamino)-3,8-dimethyl-4,14-dioxo-5,9,15-trioxatetracyclo[11.2.1.0$^{2,6}$.0$^{8,10}$]hexadec-13(16)-en-11-yl 4-fluorobenzoate;

12-(dimethylamino)-3,8-dimethyl-4,14-dioxo-5,9,15-trioxatetracyclo[11.2.1.0$^{2,6}$.0$^{8,10}$]hexadec-13(16)-en-11-yl heptanoate;

12-(dimethylamino)-3,8-dimethyl-4,14-dioxo-5,9,15-trioxatetracyclo[11.2.1.0$^{2,6}$.0$^{8,10}$]hexadec-13(16)-en-11-yl 4-(trifluoromethyl)benzoate;

12-(dimethylamino)-3,8-dimethyl-4,14-dioxo-5,9,15-trioxatetracyclo[11.2.1.0$^{2,6}$.0$^{8,10}$]hexadec-13(16)-en-11-yl 2-thiophenecarboxylate;

12-(dimethylamino)-3,8-dimethyl-4,14-dioxo-5,9,15-trioxatetracyclo[11.2.1.0$^{2,6}$.0$^{8,10}$]hexadec-13(16)-en-11-yl 3,3-dimethylbutanoate;

12-(dimethylamino)-3,8-dimethyl-4,14-dioxo-5,9,15-trioxatetracyclo[11.2.1.0$^{2,6}$.0$^{8,10}$]hexadec-13(16)-en-11-yl 1-benzothiophene-2-carboxylate;

12-(dimethylamino)-3,8-dimethyl-4,14-dioxo-5,9,15-trioxatetracyclo[11.2.1.0$^{2,6}$.0$^{8,10}$]hexadec-13(16)-en-11-yl 2-furoate;

12-(dimethylamino)-3,8-dimethyl-4,14-dioxo-5,9,15-trioxatetracyclo[11.2.1.0$^{2,6}$.0$^{8,10}$]hexadec-13(16)-en-11-yl 5-nitro-2-furoate;

12-(dimethylamino)-3,8-dimethyl-4,14-dioxo-5,9,15-trioxatetracyclo[11.2.1.02.6.0$^{8,10}$]hexadec-13(16)-en-11-yl 2-thienylacetate;

12-(dimethylamino)-3,8-dimethyl-4,14-dioxo-5,9,15-trioxatetracyclo[11.2.1.02.6.08.10]hexadec-13(16)-en-11-yl phenoxyacetate;

8-(dimethylamino)-3,10a-dimethyl-2,6-dioxodecahydro-4,7-methenofuro[3,2-c]oxireno[f]oxacycloundecin-9-yl 4-tert-butylphenylcarbamate;

8-(dimethylamino)-3,10a-dimethyl-2,6-dioxodecahydro-4,7-methenofuro[3,2-c]oxireno[f]oxacycloundecin-9-yl thien-2-ylcarbamate;

8-(dimethylamino)-3,10a-dimethyl-2,6-dioxodecahydro-4,7-methenofuro[3,2-c]oxireno[f]oxacycloundecin-9-yl 2-methoxyphenylcarbamate;

8-(dimethylamino)-3,10a-dimethyl-2,6-dioxodecahydro-4,7-metheno-furo[3,2-c]oxireno[f]oxacycloundecin-9-yl 2(methylthio)phenylcarbamate;

8-(dimethylamino)-3,10a-dimethyl-2,6-dioxodecahydro-4,7-methenofuro[3,2-c]oxireno[f]oxacycloundecin-9-yl 2-ethoxyphenylcarbamate;

8-(dimethylamino)-3,10a-dimethyl-2,6-dioxodecahydro-4,7-methenofuro[3,2-c]oxireno[f]oxacycloundecin-9-yl thien-3-ylcarbamate;

8-(dimethylamino)-3,10a-dimethyl-2,6-dioxodecahydro-4,7-methenofuro[3,2-c]oxireno[f]oxacycloundecin-9-yl 1-benzothien-3-ylcarbamate;

8-(dimethylamino)-3,10a-dimethyl-2,6-dioxodecahydro-4,7-metheno-furo[3,2-c]oxireno[f]oxacycloundecin-9-yl N-(ter-butoxycarbonyl)glycinate;

8-(dimethylamino)-3,10a-dimethyl-2,6-dioxodecahydro-4,7-methenofuro[3,2-c]oxireno[f]oxacycloundecin-9-yl thien-3-ylacetate;

8-(dimethylamino)-3,10a-dimethyl-2,6-dioxodecahydro-4,7-methenofuro[3,2-c]oxireno[f]oxacycloundecin-9-yl 1-benzothien-3-ylacetate;

8-(dimethylamino)-3,10a-dimethyl-2,6-dioxodecahydro-4,7-methenofuro[3,2-c]oxireno[f]oxacycloundecin-9-yl thiophene-3-carboxylate;

8-(dimethylamino)-3,10a-dimethyl-2,6-dioxodecahydro-4,7-methenofuro[3,2-c]oxireno[f]oxacycloundecin-9-yl 5-phenylthien-2-ylcarbamate;

8-(dimethylamino)-3,10a-dimethyl-2,6-dioxodecahydro-4,7-methenofuro[3,2-c]oxireno[f]oxacycloundecin-9-yl 1-adamantylcarbamate;

8-(dimethylamino)-3,10a-dimethyl-2,6-dioxodecahydro-4,7-methenofuro[3,2-c]oxireno[f]oxacycloundecin-9-yl 2-naphthylcarbamate;

8-(dimethylamino)-3,10a-dimethyl-2,6-dioxodecahydro-4,7-metheno-furo[3,2-c]oxireno[f]oxacycloundecin-9-yl 2-tert-butyl-6-methylphenylcarbamate;

8-(dimethylamino)-3,10a-dimethyl-2,6-dioxodecahydro-4,7-metheno-furo[3,2-c]oxireno[f]oxacycloundecin-9-yl 2,5-dimethoxyphenylcarbamate;

and a pharmaceutically acceptable salt thereof.

6. A pharmaceutical composition comprising a pharmaceutically effective amount of a compound of claim 1 and a pharmaceutically acceptable carrier.

7. A composition of claim 6, wherein the compound is selected from the group consisting of:

11-hydroxy-3,8-dimethyl-12-pyrrolidino-5,9,15-trioxatetracyclo[11.2.1.0$^{2,6}$.0$^{8,10}$]hexadec-13(16)-ene-4,14-dione;

ethyl 1-[11-hydroxy-3,8-dimethyl-4,14-dioxo-5,9,15-trioxatetracyclo[11.2.1.0$^{2,6}$.0$^{8,10}$]hexadec-13(16)-en-12-yl]-4-piperidinecarboxylate;

12-(4-benzylpiperidino)-11-hydroxy-3,8-dimethyl-5,9,15-trioxatetracyclo[11.2.1.0$^{2,6}$.0$^{8,10}$]hexadec-13(16)-ene-4,14-dione;

11-hydroxy-3,8-dimethyl-12-piperidino-5,9,15-trioxatetracyclo[11.2.1.0$^{2,6}$.0$^{8,10}$]hexadec-13(16)-ene-4,14-dione;

12-(1,4-dioxa-8-azaspiro[4.5]dec-8-yl)-11-hydroxy-3,8-dimethyl-5,9,15-trioxatetracyclo[11.2.1.0$^{2,6}$.0$^{8,10}$]hexadec-13(16)-ene-4,14-dione;

11-hydroxy-3,8-dimethyl-12-morpholino-5,9,15-trioxatetracyclo[11.2.1.0$^{2,6}$.0$^{8,10}$]hexadec-13(16)-ene-4,14-dione;

11-(tert-butyldimethylsiloxy)-12-dimethylamino-3,8-dimethyl-5,9,15-trioxatetracyclo[11.2.1.0$^{2,6}$.0$^{8,10}$]hexadec-13(16)-ene-4,14-dione;

3,8-dimethyl-12-(4-methylpiperidino)-4,14-dioxo-5,9,15-trioxatetracyclo[11.2.1.0$^{2,6}$.0$^{8,10}$]hexadec-13(16)-en-11-yl acetate;

3,8-dimethyl-12-(4-methylpiperidino)-4,14-dioxo-11-phenylcarbonyloxy-5,9,15-trioxatetracyclo[11.2.1.0$^{2,6}$.0$^{8,10}$]hexadec-13(16)-ene;

3,8-dimethyl-12-(4-methylpiperidino)-4,14-dioxo-11-phenylcarbonyloxy-5,9,15-trioxatetracyclo[11.2.1.0$^{2,6}$.0$^{8,10}$]hexadec-13(16)-ene;

ethyl 3,8-dimethyl-12-(4-methylpiperidino)-4,14-dioxo-5,9,15-trioxatetracyclo[11.2.1.0$^{2,6}$.0$^{8,10}$]hexadec-13(16)-en-11-ylcarbonate;

11-hydroxy-12-isobutylsulphanyl-3-isobutylsulphanylmethyl-8-methyl-5,9,15-trioxatetracyclo[11.2.1.0$^{2,6}$.0$^{8,10}$]hexadec-13(16)-ene-4,14-dione;

11-hydroxy-12-isobutylsulphanyl-3,8-dimethyl-5,9,15-trioxatetracyclo[11.2.1.0$^{2,6}$.0$^{8,10}$]hexadec-13(16)-ene-4,14-dione;

12-(dimethylamino)-3,8-dimethyl-4,14-dioxo-5,9,15-trioxatetracyclo[11.2.1.02.6.08.10]hexadec-13(16)-en-11-yl benzoate;

12-(dimethylamino)-3,8-dimethyl-4,14-dioxo-5,9,15-trioxatetracyclo[11.2.1.02.6.08.10]hexadec-13(16)-en-11-yl acetate;

12-(dimethylamino)-3,8-dimethyl-4,14-dioxo-5,9,15-trioxatetracyclo[11.2.1.0$^{2,6}$.0$^{8,10}$]hexadec-13(16)-en-11-yl cyclohexanecarboxylate;

12-(dimethylamino)-3,8-dimethyl-4,14-dioxo-5,9,15-trioxatetracyclo[11.2.1.0$^{2,6}$.0$^{8,10}$]hexadec-13(16)-en-11-yl 4-fluorobenzoate;

12-(dimethylamino)-3,8-dimethyl-4,14-dioxo-5,9,15-trioxatetracyclo[11.2.1.0$^{2,6}$.0$^{8,10}$]hexadec-13(16)-en-11-yl heptanoate;

12-(dimethylamino)-3,8-dimethyl-4,14-dioxo-5,9,15-trioxatetracyclo[11.2.1.0$^{2,6}$.0$^{8,10}$]hexadec-13(16)-en-11-yl 4-(trifluoromethyl)benzoate;

12-(dimethylamino)-3,8-dimethyl-4,14-dioxo-5,9,15-trioxatetracyclo[11.2.1.0$^{2,6}$.0$^{8,10}$]hexadec-13(16)-en-11-yl 2-thiophenecarboxylate;

12-(dimethylamino)-3,8-dimethyl-4,14-dioxo-5,9,15-trioxatetracyclo[11.2.1.0$^{2,6}$.0$^{8,10}$]hexadec-13(16)-en-11-yl 3,3-dimethylbutanoate;

12-(dimethylamino)-3,8-dimethyl-4,14-dioxo-5,9,15-trioxatetracyclo[11.2.1.0$^{2,6}$.0$^{8,10}$]hexadec-13(16)-en-11-yl 1-benzothiophene-2-carboxylate;

12-(dimethylamino)-3,8-dimethyl-4,14-dioxo-5,9,15-trioxatetracyclo[11.2.1.0$^{2,6}$.0$^{8,10}$]hexadec-13(16)-en-11-yl 2-furoate;

12-(dimethylamino)-3,8-dimethyl-4,14-dioxo-5,9,15-trioxatetracyclo[11.2.1.0$^{2,6}$.0$^{8,10}$]hexadec-13(16)-en-11-yl 5-nitro-2-furoate;

12-(dimethylamino)-3,8-dimethyl-4,14-dioxo-5,9,15-trioxatetracyclo[11.2.1.02.6.08.10]hexadec-13(16)-en-11-yl 2-thienylacetate;

12-(dimethylamino)-3,8-dimethyl-4,14-dioxo-5,9,15-trioxatetracyclo[11.2.1.02.6.08.10]hexadec-13(16)-en-11-yl phenoxyacetate;

8-(dimethylamino)-3.10a-dimethyl-2,6-dioxodecahydro-4,7-methenofuro[3,2-c]oxireno[f]oxacycloundecin-9-yl 4-tert-butylphenylcarbamate;

8-(dimethylamino)-3.10a-dimethyl-2,6-dioxodecahydro-4,7-methenofuro[3,2-c]oxireno[f]oxacycloundecin-9-yl thien-2-ylcarbamate;

8-(dimethylamino)-3.10a-dimethyl-2,6-dioxodecahydro-4,7-methenofuro[3,2-c]oxireno[f]oxacycloundecin-9-yl 2-methoxyphenylcarbamate;

8-(dimethylamino)-3.10a-dimethyl-2,6-dioxodecahydro-4,7-metheno-furo[3,2-c]oxireno[f]oxacycloundecin-9-yl 2(methylthio)phenylcarbamate;

8-(dimethylamino)-3.10a-dimethyl-2,6-dioxodecahydro-4,7-methenofuro[3,2-c]oxireno[f]oxacycloundecin-9-yl 2-ethoxyphenylcarbamate;

8-(dimethylamino)-3.10a-dimethyl-2,6-dioxodecahydro-4,7-methenofuro[3,2-c]oxireno[f]oxacycloundecin-9-yl thien-3-ylcarbamate;

8-(dimethylamino)-3.10a-dimethyl-2,6-dioxodecahydro-4,7-methenofuro[3,2-c]oxireno[f]oxacycloundecin-9-yl 1-benzothien-3-ylcarbamate;

8-(dimethylamino)-3.10a-dimethyl-2,6-dioxodecahydro-4,7-metheno-furo[3,2-c]oxireno[f]oxacycloundecin-9-yl N-(ter-butoxycarbonyl)glycinate;

8-(dimethylamino)-3.10a-dimethyl-2,6-dioxodecahydro-4,7-methenofuro[3,2-c]oxireno[f]oxacycloundecin-9-yl thien-3-ylacetate;

8-(dimethylamino)-3.10a-dimethyl-2,6-dioxodecahydro-4,7-methenofuro[3,2-c]oxireno[f]oxacycloundecin-9-yl 1-benzothien-3-ylacetate;

8-(dimethylamino)-3.10a-dimethyl-2,6-dioxodecahydro-4,7-methenofuro[3,2-c]oxireno[f]oxacycloundecin-9-yl thiophene-3-carboxylate;

8-(dimethylamino)-3.10a-dimethyl-2,6-dioxodecahydro-4,7-methenofuro[3,2-c]oxireno[f]oxacycloundecin-9-yl 5-phenylthien-2-ylcarbamate;

8-(dimethylamino)-3.10a-dimethyl-2,6-dioxodecahydro-4,7-methenofuro[3,2-c]oxireno[f]oxacycloundecin-9-yl 1-adamantylcarbamate;

8-(dimethylamino)-3.10a-dimethyl-2,6-dioxodecahydro-4,7-methenofuro[3,2-c]oxireno[f]oxacycloundecin-9-yl 2-naphthylcarbamate;

8-(dimethylamino)-3.10a-dimethyl-2,6-dioxodecahydro-4,7-metheno-furo[3,2-c]oxireno[f]oxacycloundecin-9-yl 2-tert-butyl-6-methylphenylcarbamate;

8-(dimethylamino)-3.10a-dimethyl-2,6-dioxodecahydro-4,7-metheno-furo[3,2-c]oxireno[f]oxacycloundecin-9-yl 2,5-dimethoxyphenylcarbamate;

or a pharmaceutically acceptable salt of one of the latter.

8. A method of treating cancer in warm-blooded animals comprising administering to warm-blooded animals in need thereof a tumor inhibiting amount of a compound of claim 1.

9. A method of treating viral infections or diseases in warm-blooded animals comprising administering to warm-blooded animals in need thereof an amount of a compound of claim 1 sufficient to treat viral infections or diseases.

10. A method of treating conditions selected from the group consisting of atherosclerosis, benign hyperplasia of the prostate and fibroses in warm-blooded animals comprising administrating to warm-blooded animals in need thereof an amount of a compound of claim 1 sufficient to treat said conditions.

11. A method of treating viral infections in warm-blooded animals comprising administering to warm-blooded animals in need thereof an antivirally effective amount of a compound of claim 1.

12. A method of treating bacterial infections in warm-blooded animals comprising administering to warm-blooded animals in need thereof a bactericidally effective amount of a compound of claim 1.

13. A method of treating parasitic infection in warm-blooded animals comprising administering to warm-blooded animals in need thereof a parasitically effective amount of a compound of claim 1.

* * * * *